United States Patent
Hinrichs et al.

(10) Patent No.: US 11,077,182 B2
(45) Date of Patent: Aug. 3, 2021

(54) METHODS OF PREPARING ANTI-HUMAN PAPILLOMAVIRUS ANTIGEN T CELLS

(71) Applicant: The United States of America, as represented by the Secretary, Department of Health and Human Services, Bethesda, MD (US)

(72) Inventors: Christian S. Hinrichs, Bethesda, MD (US); Steven A. Rosenberg, Potomac, MD (US)

(73) Assignee: The United States of Americans represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 17/113,570

(22) Filed: Dec. 7, 2020

(65) Prior Publication Data
US 2021/0121559 A1 Apr. 29, 2021

Related U.S. Application Data

(63) Continuation of application No. 16/218,658, filed on Dec. 13, 2018, which is a continuation of application No. 14/905,138, filed as application No. PCT/US2014/046478 on Jul. 14, 2014, now abandoned.

(60) Provisional application No. 61/846,161, filed on Jul. 15, 2013.

(51) Int. Cl.
| | | |
|---|---|---|
| C12N 5/00 | (2006.01) | |
| A61K 39/00 | (2006.01) | |
| A61K 35/17 | (2015.01) | |
| A61K 39/12 | (2006.01) | |
| C12N 5/0783 | (2010.01) | |
| C12N 7/00 | (2006.01) | |

(52) U.S. Cl.
CPC .............. *A61K 39/12* (2013.01); *A61K 35/17* (2013.01); *C12N 5/0636* (2013.01); *C12N 5/0638* (2013.01); *C12N 7/00* (2013.01); *A61K 2039/5158* (2013.01); *A61K 2039/572* (2013.01); *A61K 2039/585* (2013.01); *C12N 2501/2302* (2013.01); *C12N 2502/30* (2013.01); *C12N 2710/20011* (2013.01)

(58) Field of Classification Search
None
See application file for complete search history.

(56) References Cited

U.S. PATENT DOCUMENTS

| 8,034,334 B2 | 10/2011 | Dudley et al. |
| 8,383,099 B2 * | 2/2013 | Dudley .............. A61K 38/2046 424/93.7 |
| 2011/0052530 A1 | 3/2011 | Dudley et al. |
| 2012/0244133 A1 | 9/2012 | Rosenberg et al. |

OTHER PUBLICATIONS

Santin et al. Induction of tumor-specific cytotoxicity in tumor infiltrating lymphocytes by HPV16 and HPV18 E7-pulsed autologous dendritic cells in patients with cancer of the uterine cervix. Gynecol Oncol. May 2003;89(2):271-80.*
Ramos et al. Human Papillomavirus Type 16 E6/E7-specific Cytotoxic T Lymphocytes for Adoptive Immunotherapy of HPV-associated Malignancies. J Immunother, vol. 36, No. 1, Jan. 2013, pp. 66-76.*
"A Phase II Study of Lymphodepletion Followed by Autologus Tumor-Infiltrating Lymphocytes and High-Dose Adesleukin for Human Papillomavirus-Associated Cancers," ClinicalTrials.gov, retrieved from http://clinicaltrials.gov/ct2/show/record/NCT01585428 (2012).
Cruz et al., "Adverse events following infusion of T cells for adoptive immunotherapy: a 10-year experience," *Cytotherapy*, 12(6): 743-749 (2010).
De Jong et al., "Rapid enrichment of human papillomavirus (HPV)-specific polyclonal T cell populations for adoptive immunotherapy of cervical cancer," *Int. J. Cancer*, 114(2): 274-82 (2005).
Dengler, Roni, "Cancer immunotherapy company tries to explain deaths in recent trial," *Science*, doi:10.1126/science.aar5192; 4 sheets (Nov. 16, 2017).
Dudley et al., "A phase I study of non myeloablative chemotherapy and adoptive transfer of autologous tumor antigen-specific T lymphocytes in patients with metastatic melanoma," *J. Immunother*, 25(3): 243-251 (2002).
Dudley et al., "Generation of Tumor-Infiltrating Lymphocyte Cultures for Use in Adoptive Transfer Therapy for Melanoma Patients," *J. Immunother.*, 26: 332-42 (2003).
Evans, et al., "Infiltration of Cervical Cancer Tissue with Human Papillomavirus-specific Cytotoxic T-Lymphocytes," *Cancer Research*, 57: 2943-2950 (1997).
Geukes Foppen et al., "Tumor-infiltrating lymphocytes for the treatment of metastatic cancer," *Mol. Oncol.*, 9(10): 1918-1935 (2015).
Heemskerk et al., "Adoptive Cell Therapy for Patients with Melanoma, Using Tumor-Infiltrating Lymphocytes Genetically Engineered to Secrete Interleukin-2," *Hum Gene Ther*. 19(5): 496-510 (2008).
Heusinkveld et al., "Systemic and local human papillomavirus 16-specific T-cell immunity in patients with head and neck cancer," *International Journal of Cancer*, 131(2): E74-E85 (2012).

(Continued)

*Primary Examiner* — Nianxiang Zou
(74) *Attorney, Agent, or Firm* — Leydig, Voit & Mayer

(57) ABSTRACT

Disclosed are methods of preparing an isolated population of human papillomavirus (HPV)-specific T cells comprise dividing an HPV-positive tumor sample into multiple fragments; separately culturing the multiple fragments; obtaining T cells from the cultured multiple fragments; testing the T cells for specific autologous HPV-positive tumor recognition; selecting the T cells that exhibit specific autologous HPV-positive tumor recognition; and expanding the number of selected T cells to produce a population of HPV-specific T cells for adoptive cell therapy. Related methods of treating or preventing cancer using the T cells are also disclosed.

24 Claims, 26 Drawing Sheets

(56) References Cited

OTHER PUBLICATIONS

Hilders et al., "Isolation and characterization of tumor-infiltrating lymphocytes from cervical carcinoma," *International Journal of Cancer*, 57(6): 805-813 (1994).
Hinrichs, "T cell Therapy for Human Papillomavirus-Associated Cancers," presentation at Walter Reed-National Naval Medical Center Gynecological Oncology Conference (Nov. 6, 2012).
International Bureau, International Search Report in Application No. PCT/US2014/046478, dated Oct. 14, 2014.
"Head and Neck Cancers," *NIH National Cancer Institute*, accessed online at <cancer.gov/types/head-and-neck/head-neck-fact-sheet>, on Aug. 27, 2019.
International Bureau, Written Opinion in Application No. PCT/US2014/046478, dated Oct. 14, 2014.
Jin et al., "Simplified Method of the Growth of Human Tumor Infiltrating Lymphocytes in Gas-permeable Flasks to Numbers Needed for Patient Treatment," *J. Immunother.*, 35(3): 283-92 (2012).
Johnson et al., "Gene therapy with human and mouse T-cell receptors mediates cancer regression and targets normal tissues expressing cognate antigen," *Blood* 114: 535-46 (2009).
June, "Principles of adoptive T cell cancer therapy," *J. Clin. Invest.*, 117: 1204-1212 (2007).
Nasman et al., "Tumor infiltrating CD8+ and Foxp3+ lymphocytes correlate to clinical outcome and human papillomavirus (HPV) status in tonsillar cancer," *PLoS One*, 7(6): e38711 (2012).
"NCI Dictionary of Cancer—Primary Tumor," *NIH National Cancer Institute*, accessed online at <cancer.gov/publications/dictionaries/cancer-terms/def/primary-tumor>, on Aug. 27, 2019.
Ngler, R., "Cancer immunotherapy company tries to explain deaths in recent trial," *Science*, doi:10.1126/science.aar5192; 4 sheets (Nov. 16, 2017).
Piersma et al., "Human papilloma virus specific T cells infiltrating cervical cancer and draining lymph nodes show remarkably frequent use of HLA-DQ and -DP as a restriction element," *Int. J. Cancer*, 122: 486-94 (2008).
Pilch et al., "Antigen-Driven T-Cell Selection in Patients with Cervical Cancer as Evidenced by T-Cell Receptor Analysis and Recognition of Autologous Tumor," *Clin. Diagn. Lab. Immunol.*, 9(2): 267-78 (2002).
Ramos et al., "Human papillomavirus type 16 E6/E7-specific cytotoxic T lymphocytes for adoptive immunotherapy of HPV-associated malignancies," *J. Immunother.*, 36(1): 66-76 (2013).
Riddell et al., "The use of anti-CD3 and anti-CD28 monoclonal antibodies to clone and expand human antigen-specific T-cells," *J. Immunol. Methods*, 128: 189-201 (1990).
Rosenberg et al., "Durable Complete Responses in Heavily Pretreated Patients with Metastatic Melanoma Using T-Cell Transfer Immunotherapy," *Clinical Cancer Research*, 17(13): 4550-4557 (2011).
Santin et al., "Induction of tumor-specific cytotoxicity in tumor infiltrating lymphocytes by HPV16 and HPV18 E7-pulsed autologous dendritic cells in patients with cancer of the uterine cervix," *Gynecol. Oncol.*, 89(2): 271-80 (2003).
Sin et al., "Adoptive Transfer of Human Papillomavirus E7-specific CTL Enhances Tumor Chemoresponse Through the Perforin/Granzyme-mediated Pathway," *Mol. Ther.*, 17(5): 906-13 (2009).
Stevanović et al., "A phase II study of tumor-infiltrating lymphocyte therapy for human papillomavirus-associated epithelial cancers," *Clin. Cancer Res.*, 25(5): 1486-1493 (2019).
Van Steenwijk et al., "An Unexpectedly Large Polyclonal Repertoire of HPV-Specific T Cells is Poised for Action in Patients with Cervical Cancer," *Cancer Res.*, 70(7): 2707-17 (2010).
Wolfl et al., "Activation-induced expression of CD137 permits detection, isolation, and expansion of the full repertoire of CD8+ T cells responding to antigen without requiring knowledge of epitope specificities," *Blood*, 110(1): 201-10 (2007).
Zhou et al., "Towards Curative Cancer Immunotherapy: Overcoming Posttherapy Tumor Escape," *Clin. Dev. Immunol.*, 2012: 1-12 (2012).
Yee, C., "Adoptive T cell therapy: Addressing challenges in cancer immunotherapy," *J. Transl. Med.*, 3(1): 17, pp. 8 (2005).

* cited by examiner

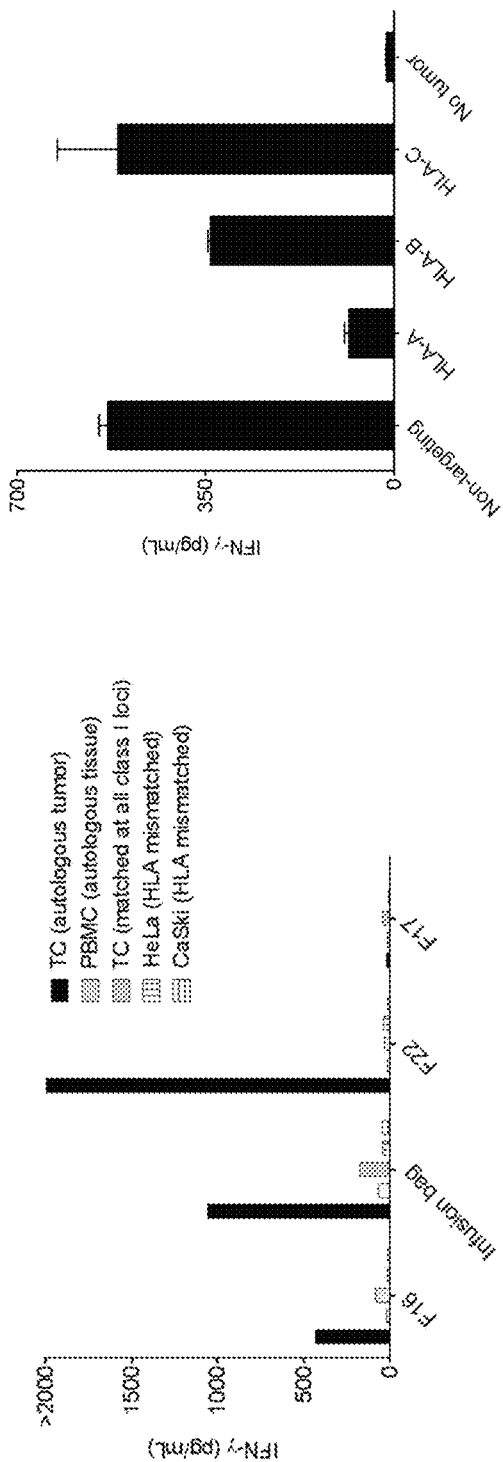
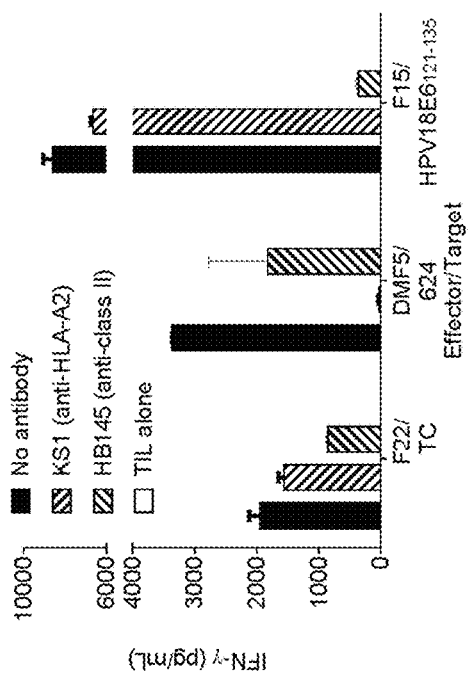
FIG. 2A
FIG. 2B
FIG. 2C

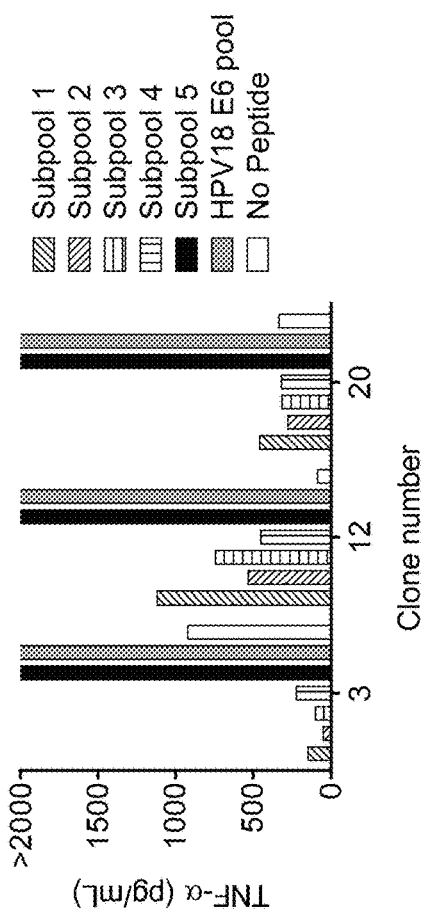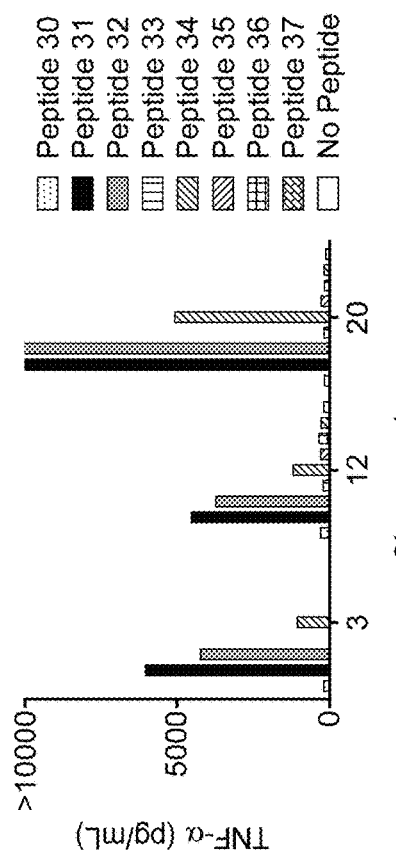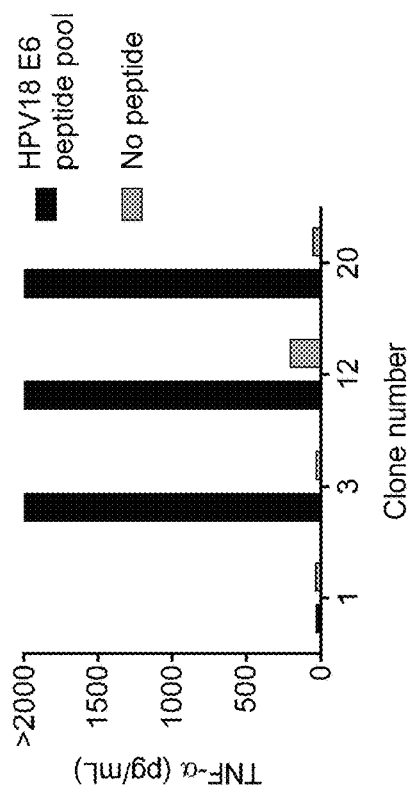
FIG. 7A
FIG. 7B
FIG. 7C

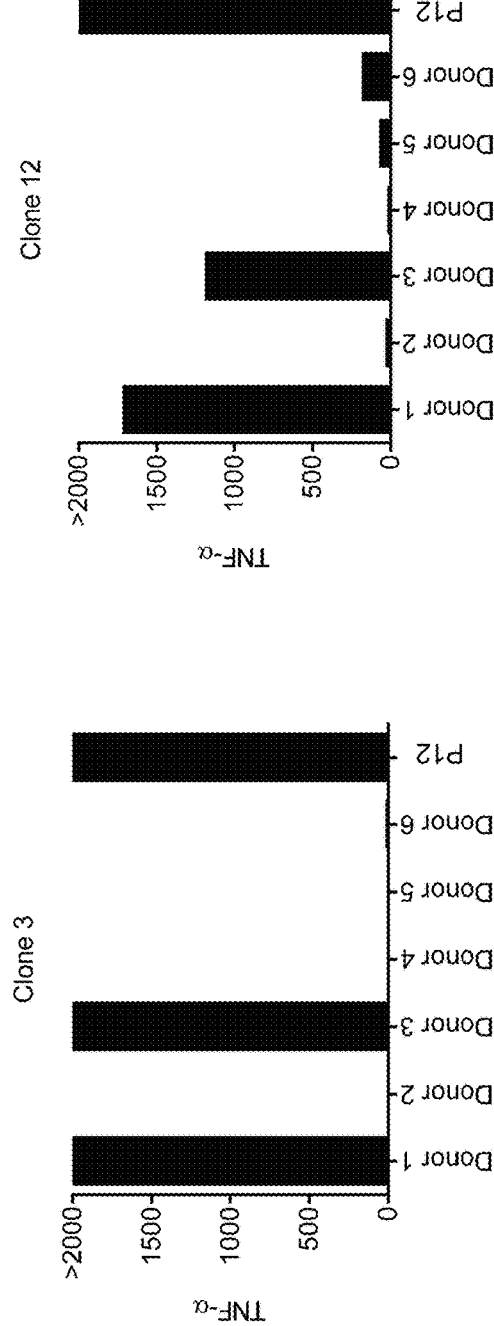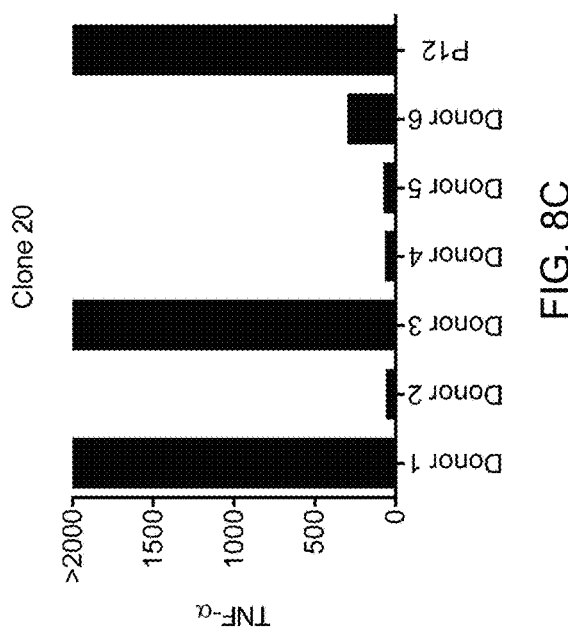
FIG. 8A
FIG. 8B
FIG. 8C

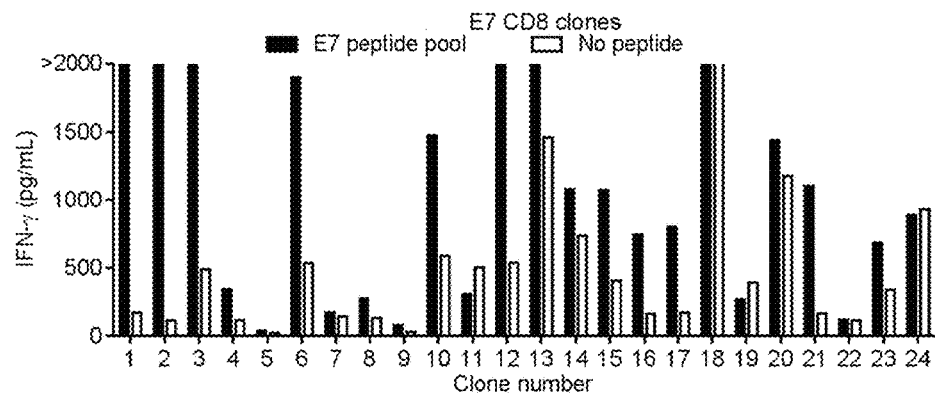
FIG. 11A
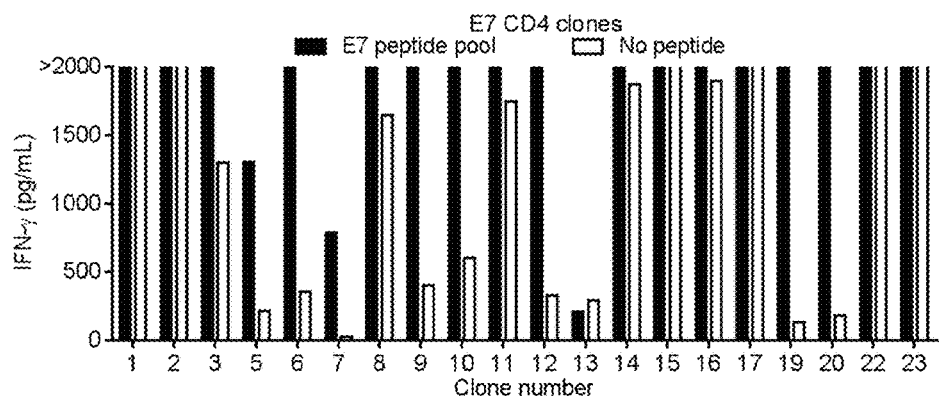
FIG. 11B
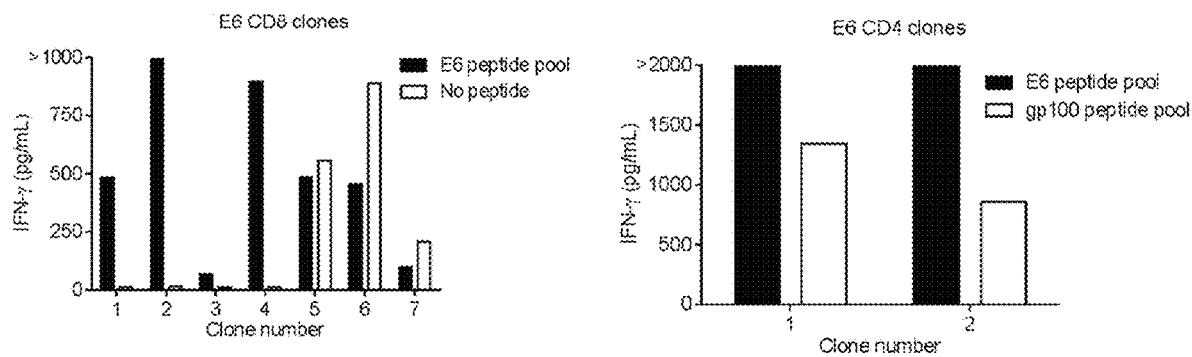
FIG. 11C
FIG. 11D

FIG. 16A
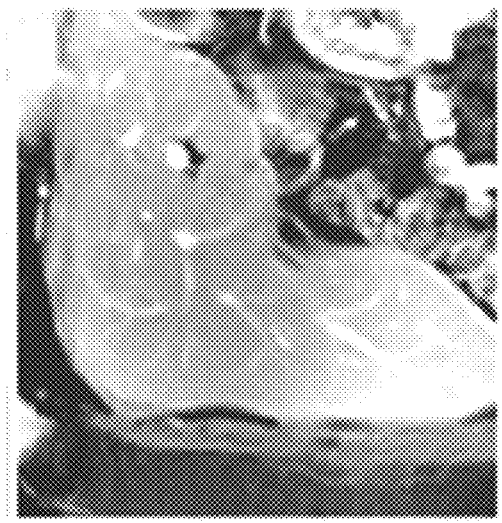
FIG. 16B
FIG. 16C
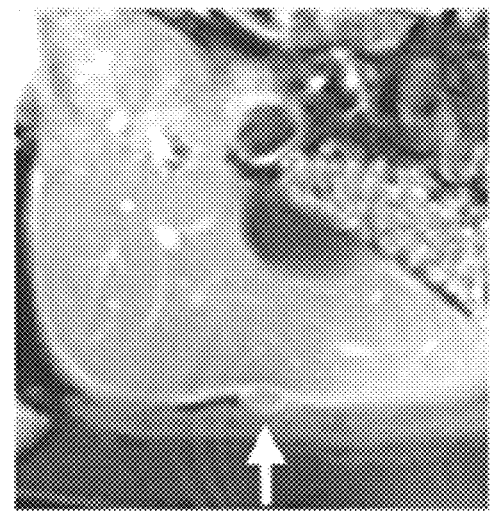
FIG. 16D

METHODS OF PREPARING ANTI-HUMAN PAPILLOMAVIRUS ANTIGEN T CELLS

CROSS-REFERENCE TO RELATED APPLICATIONS

This patent application is a continuation of U.S. application Ser. No. 16/218,658, filed Dec. 13, 2018, which is a continuation of U.S. application Ser. No. 14/905,138, filed Jan. 14, 2016, now abandoned, which is the U.S. national phase of International Patent Application No. PCT/US2014/046478, filed Jul. 14, 2014, which claims the benefit of U.S. Provisional Patent Application No. 61/846,161, filed Jul. 15, 2013, each of which is incorporated herein by reference in its entirety.

STATEMENT REGARDING FEDERALLY SPONSORED RESEARCH AND DEVELOPMENT

This invention was made with Government support under project number BC010984-05 by the National Institutes of Health, National Cancer Institute. The Government has certain rights in the invention.

BACKGROUND OF THE INVENTION

The primary cause of some cancer types such as, for example, uterine cervical cancer, is human papillomavirus (HPV) infection. Despite advances in treatments such as chemotherapy, the prognosis for many cancers, including HPV-associated cancers, may be poor. Accordingly, there exists an unmet need for additional treatments for cancer, particularly HPV-associated cancers.

BRIEF SUMMARY OF THE INVENTION

An embodiment of the invention provides a method of preparing a population of HPV-specific T cells, the method comprising: dividing an HPV-positive tumor sample into multiple fragments; separately culturing the multiple fragments in the presence of only one cytokine; obtaining T cells from the cultured multiple fragments; testing the T cells for one or both of specific autologous HPV-positive tumor recognition and HPV antigen recognition; selecting the T cells that exhibit one or both of specific autologous HPV-positive tumor recognition and HPV antigen recognition; and expanding the number of selected T cells to produce a population of HPV-specific T cells.

Another embodiment of the invention provides a method of preparing a population of HPV-specific T cells, the method comprising: dividing an HPV-positive tumor sample into multiple fragments; separately culturing the multiple fragments; obtaining T cells from the cultured multiple fragments; testing the T cells for one or both of specific autologous HPV-positive tumor recognition and HPV antigen recognition; selecting the T cells that exhibit one or both of specific autologous HPV-positive tumor recognition and HPV antigen recognition; and expanding the number of selected T cells using one or both of (i) OKT3 antibody and (ii) interleukin (IL)-2 to produce a population of HPV-specific T cells.

Still another embodiment of the invention provides a method of treating or preventing cancer in a mammal, the method comprising: dividing an HPV-positive tumor sample into multiple fragments; separately culturing the multiple fragments; obtaining T cells from the cultured multiple fragments; testing the T cells for one or both of specific autologous HPV-positive tumor recognition and HPV antigen recognition; selecting the T cells that exhibit one or both of specific autologous HPV-positive tumor recognition and HPV antigen recognition; expanding the number of selected T cells to produce a population of HPV-specific T cells for adoptive cell therapy; and administering the expanded number of T cells to the mammal in an amount effective to treat or prevent cancer in the mammal.

BRIEF DESCRIPTION OF THE SEVERAL VIEWS OF THE DRAWINGS

FIG. 2A is a graph showing IFN-γ (pg/mL) secreted by effector TIL generated from tumor fragment F16, F17, or F22 of Patient 1, or by the cells given to the patient for treatment ("infusion bag") upon co-culture with target autologous tumor cells (shaded bars), peripheral blood mononuclear cells (PBMC) from autologous tissue (forward slash hatched bars), tumor cells matched at all class I loci (backslash hatched bars), HLA-mismatched HeLa cells (vertical striped bars), or HLA-mismatched CaSki cells (horizontal striped bars).

FIG. 2B is a graph showing IFN-γ (pg/mL) secreted by effector TIL from Patient 1 cultured alone (no tumor) or upon co-culture with autologous tumor cells that were transfected with silencing RNA against HLA-A, HLA-B, HLA-C, or RNA against an irrelevant target (non-targeting).

FIG. 2C is a graph showing IFN-γ (pg/mL) secreted by effector TIL upon co-culture with target cells (effector/targets: Patient 1 TIL/autologous tumor cells; DMF5/624 cells; or F15/HPV18E6$_{121-135}$) without antibody (black bars), with anti-HLA-A2 antibody (back slash hatched bars), or with anti-Class II antibody (forward slash hatched bars). White bars indicate effector cells cultured alone.

FIG. 7A is a graph showing tumor necrosis factor (TNF) α (pg/mL) secreted by clones 1, 3, 12, and 20 upon culture alone (grey bars) or with an HPV18 E6 peptide pool (black bars).

FIG. 7B is a graph showing TNFα (pg/mL) secreted by clones 3, 12, and 20 upon culture alone (white bars) or with an HPV18 E6 peptide pool (grey bars) or with HPV 18 E6 peptide subpool 1 (forward slash hatched bars), subpool 2 (back slash hatched bars), subpool 3 (horizontal striped bars), subpool 4 (vertical striped bars), or subpool 5 (black bars).

FIG. 7C is a graph showing TNFα (pg/mL) secreted by clones 3, 12, and 20 upon culture alone (white bars) or with an HPV18 E6 peptide 30 (dotted bars), peptide 31 (black bars), peptide 32 (grey bars), peptide 33 (vertical striped bars), peptide 34 (forward slash hatched bars), peptide 35 (back slash hatched bars), peptide 36 (squared bars), or peptide 37 (herringbone bars).

FIGS. 8A-8C are graphs showing TNFα (pg/mL) secreted by clones 3 (A), 12 (B), and 20 (C) upon co-culture with autologous PBMC (P12) or PBMC from one of Donors 1-6.

FIG. 11A is a graph showing IFN-γ (pg/mL) secreted by CD8 positive effector TIL clones from Patient 4 upon co-culture with dendritic cells pulsed with an HPV 16 E7 peptide pool (shaded bars) or no peptide (unshaded bars).

FIG. 11B is a graph showing IFN-γ (pg/mL) secreted by CD4 positive effector TIL clones from Patient 4 upon co-culture with dendritic cells pulsed with an HPV 16 E7 peptide pool (shaded bars) or no peptide (unshaded bars).

FIG. 11C is a graph showing IFN-γ (pg/mL) secreted by CD8 positive effector TIL clones from Patient 4 upon co-culture with dendritic cells pulsed with an HPV 16 E6 peptide pool (shaded bars) or no peptide (unshaded bars).

FIG. 11D is a graph showing IFN-γ (pg/mL) secreted by CD4 positive effector TIL clones from Patient 4 upon co-culture with dendritic cells pulsed with an HPV 16 E6 peptide pool (shaded bars) or no peptide (unshaded bars).

FIGS. 16A-D are delayed gadolinium-enhanced T1-weighted MRI images of Patient 8. A and C each show a tumor on the liver surface before treatment. B and D show that neither tumor was present 11 months following treatment. Arrows in A and C indicate locations of the tumors.

DETAILED DESCRIPTION OF THE INVENTION

Figure 1A:
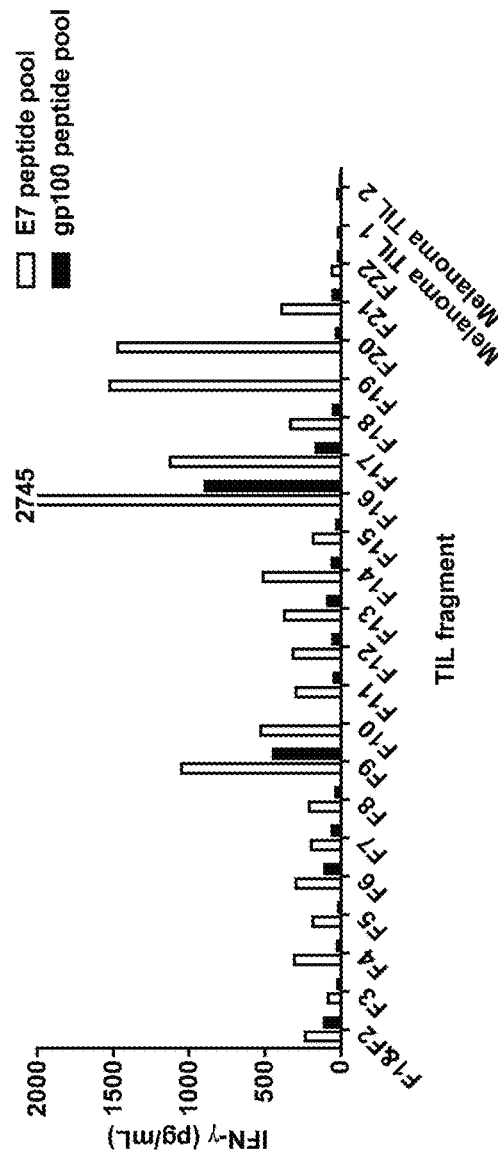
FIG. 1A is a graph showing interferon gamma (IFN-γ) (pg/mL) secreted by effector tumor infiltrating lymphocytes (TIL) generated from 22 tumor fragments (F1-F22) from Patient 1 or melanoma TIL upon co-culture with a target gp100 peptide pool (shaded bars) or an HPV 18 E7 peptide pool (unshaded bars).

It has been discovered that populations of human papillomavirus (HPV)-specific T cells can be prepared for a variety of applications, for example, adoptive cell therapy. The inventive methods may generate cells that are useful for treating a variety of conditions, e.g., cancer.

The inventive methods provide numerous advantages. For example, the inventive methods may, advantageously, generate T cells from HPV-positive cancers at a grade and scale suitable for clinical use. Additionally, the inventive methods may, advantageously, generate T cells that recognize the HPV antigens E6 and E7, which are constitutively and specifically expressed by cancer cells and are not expressed by normal cells. Therefore, without being bound to a particular theory or mechanism, it is believed that T cells generated by the inventive methods advantageously target the destruction of cancer cells while minimizing or eliminating the destruction of normal, non-cancerous cells, thereby reducing, for example, by minimizing or eliminating, toxicity. In addition, because an embodiment of the inventive methods includes nonmyeloablative chemotherapy, the inventive methods can advantageously be used to treat patients that would not be eligible for treatments that involve total body irradiation (TBI) such as, for example, patients that have already undergone myeloablative therapy, e.g., radiotherapy, prior to treatment; patients with comorbid conditions; and patients with less than $2 \times 10^6$ CD34$^+$ cells/kg. Moreover, the inventive methods of treating cancer may, advantageously, successfully treat or prevent HPV-positive cancers that do not respond to other types of treatment such as, for example, chemotherapy alone, surgery, or radiation.

An embodiment of the invention comprises obtaining an HPV-positive tumor sample from a mammal. The tumor sample may be obtained from a mammal in any suitable manner such, for example, biopsy or surgical resection.

In an embodiment, the method may comprise testing the tumor sample for HPV infection. The HPV may be any HPV subtype. Preferably, the HPV subtype is HPV 16 or HPV 18. The testing may comprise testing for the expression of any protein (e.g., an antigen) specifically expressed by HPV-infected cells such as, for example, any one or more of HPV 16 E6, HPV 16 E7, HPV 18 E6, and HPV 18 E7, expression of any RNA encoding the HPV-specific protein, or a combination thereof. Testing for HPV infection may be carried out in any suitable manner known in the art. Exemplary HPV tests may include any one or more of reverse transcriptase (RT) polymerase chain reaction (PCR)-based genotyping and Western blots. The tumor sample may be positive for any subtype of HPV infection such as, for example, HPV 16 or HPV 18 infection.

An embodiment of the invention comprises dividing the HPV-positive tumor sample into multiple fragments. The tumor sample may be divided into any suitable number of fragments such as, for example, 4, 8, 12, 16, 20, 24, 28, 32, 36, 40 or more fragments. Preferably, the tumor sample is divided into 24 fragments. The tumor sample may be divided in any suitable manner e.g., mechanically (disaggregating the tumor using, e.g., a gentleMACS™ Dissociator, Miltenyi Biotec, Auburn, Calif.) or enzymatically (e.g., collagenase or DNase).

An embodiment of the invention comprises separately culturing the multiple fragments. In this regard, the fragments may be cultured in separate containers, e.g., separate plates or separate wells of a plate. The multiple fragments may be cultured in any suitable manner. For example, the fragments may be cultured in a gas permeable container as described in U.S. Patent Application Publication No. 2012/0244133. In an embodiment of the invention, the tumor fragments are cultured in the presence of a combination of two or more cytokines. In a preferred embodiment, however, the method comprises culturing the tumor fragments in the presence of only one cytokine. The cytokine may be any suitable cytokine such as, for example, interleukin (IL)-2, IL-7, IL-15, or IL-12. Preferably, the cytokine is IL-2. The tumor fragments may be cultured in any suitable amount of cytokine (e.g., from about 30 IU/mL to about 6,000 IU/mL, preferably about 6,000 IU/mL). Preferably, the method comprises culturing tumor fragments in about 6,000 IU/mL IL-2.

The method may comprise obtaining T cells from the cultured multiple fragments. The method may comprise culturing the T cells until confluence (e.g., about $2\times10^6$ lymphocytes per mL in a 24-well plate), e.g., from about 12 to about 28 days.

The method may comprise testing the T cells for one or both of specific autologous HPV-positive tumor recognition and HPV antigen recognition. Specific autologous HPV-positive tumor recognition can be tested by any method known in the art, e.g., by measuring cytokine release (e.g., interferon (IFN)-γ) following co-culture with autologous HPV-positive tumor cells. T cells may be considered to recognize HPV-positive tumor if, for example, co-culture with autologous HPV-positive tumor cells results in IFN-γ release that is one or more of (i) twice the amount of IFN-γ that is measured when the T cells are cultured alone (background); (ii) at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more); and (iii) blocked by MHC Class I antibody by greater than about 40%, greater than about 50%, or greater than about 60%.

Specific HPV antigen recognition can be tested by any method known in the art, e.g., by measuring cytokine release (e.g., IFN-γ) following co-culture with antigen-negative antigen presenting cells (e.g., dendritic cells) that have been pulsed with a peptide of an HPV antigen. T cells may be considered to recognize HPV antigen if, for example, IFN-γ release is one or both of (i) twice the amount of IFN-γ that is measured when the T cells are cultured with antigen presenting cells that are pulsed with a negative control peptide and (ii) at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of IFN-γ upon co-culture with antigen-negative antigen presenting cells pulsed with a low concentration of HPV 16 or HPV 18 peptide (e.g., about 0.05 ng/mL to about 5 ng/mL, 0.05 ng/mL, 0.1 ng/mL, 0.5 ng/mL, 1 ng/mL, or 5 ng/mL). The T cells may also secrete IFN-γ upon co-culture with antigen-negative antigen presenting cells pulsed with higher concentrations of HPV peptide.

The HPV antigen may be any HPV antigen. For example, the HPV antigen may be any one or more of HPV 16 E6, HPV 16 E7, HPV 18 E6, and HPV 18 E7. While in some embodiments, the population of T cells may specifically recognize only one HPV antigen, in some embodiments, the population of T cells may specifically recognize more than one HPV antigen. In this regard, the population of T cells may comprise multiple T cells each having different HPV specificities. For example, the population of T cells may include some T cells that specifically recognize HPV 16 E6 and other T cells that specifically recognize HPV 16 E7, or the population may include some T cells that specifically recognize HPV 18 E6 and other T cells that specifically recognize HPV 18 E7.

The method may comprise selecting the T cells that exhibit one or both of specific autologous HPV-positive tumor recognition and HPV antigen recognition. In an embodiment of the invention, while testing the T cells for one or both of specific autologous HPV-positive tumor recognition and HPV antigen recognition may identify those cultures that contain T cells that recognize HPV, those cultures that contain the HPV-reactive T cells may also contain additional T cells that are reactive against other, non-HPV tumor antigens. Accordingly, the selected population of T cells may include polyclonal T cells with multiple specificities. In another embodiment of the invention, the testing identifies cultures that only contain T cells that recognize HPV. In this regard, the selected population of T cells may include T cells with only HPV specificity.

The method may further comprise expanding the number of selected T cells to produce a population of HPV-specific T cells. Rapid expansion provides an increase in the number of antigen-specific T-cells of at least about 100-fold (or 200-, 300-, 400-, 500-, 600-, 700-, 800-, 900-fold, or greater) over a period of about 10 to about 14 days, preferably about 14 days. More preferably, rapid expansion provides an increase of at least about 1000-fold (or 1500-, 2000-, 2500-, 3000-fold, or greater) over a period of about 10 to about 14 days, preferably about 14 days. Most preferably, rapid expansion provides an increase of at least about 1000-fold to about 3000-fold over a period of about 10 to about 14 days, preferably about 14 days.

Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). For example, the numbers of T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/mL of OKT3, a mouse monoclonal anti-CD3 antibody (available from Ortho-McNeil, Raritan, N.J.). Alternatively, the number of T cells can be rapidly expanded by stimulation in vitro with an antigen (one or more, including antigenic portions thereof, such as epitope(s), or a cell) of the cancer, which can be optionally expressed from a vector, e.g., 0.3 μM MART-1:26-35 (27L) or gp100:209-217 (210M), in the presence of a T-cell growth factor, such as 300 IU/mL IL-2 or IL-15, with IL-2 being preferred. The numbers of in vitro-induced T-cells may be rapidly expanded by re-stimulation with the same antigen(s) of the cancer pulsed onto antigen-presenting cells. In an embodiment, the numbers of T cells are expanded in a gas permeable container as described in U.S. Patent Application Publication No. 2012/0244133.

In an embodiment of the invention, the method comprises expanding the number of T cells using one or both of (i) irradiated allogeneic feeder cells and (ii) irradiated autologous feeder cells and one or both of (iii) OKT3 antibody and (iv) a T-cell growth factor, such as IL-2 or IL-15, with IL-2 being preferred. The method may comprise expanding the number of T cells using one or both of (i) irradiated allogeneic feeder cells and (ii) irradiated autologous feeder cells and one or both of (iii) OKT3 antibody and (iv) interleukin (IL)-2. Preferably, the method comprises expanding the number of T cells using one or both of (i) irradiated allogeneic feeder cells and (ii) irradiated autologous feeder cells and both of (iii) OKT3 antibody and (iv) interleukin (IL)-2. In an especially preferred embodiment, the method comprises expanding the number of T cells using (i) irradiated allogeneic feeder cells, (ii) OKT3 antibody and (iii) interleukin (IL)-2.

In still another embodiment, the method comprises expanding the number of selected T cells using one or both of (i) OKT3 antibody and (ii) interleukin (IL)-2 to produce a population of HPV-specific T cells, optionally in combination with one or both of irradiated allogeneic feeder cells and irradiated autologous feeder cells. In this regard, an embodiment of the invention provides a method of preparing a population of HPV-specific T cells, the method comprising: dividing an HPV-positive tumor sample into multiple fragments; separately culturing the multiple fragments; obtaining T cells from the cultured multiple fragments; testing the T cells for one or both of specific autologous HPV-positive tumor recognition and HPV antigen recognition; selecting the T cells that exhibit one or both of specific autologous HPV-positive tumor recognition and HPV antigen recognition; and expanding the number of selected T cells using one or both of (i) OKT3 antibody and (ii) interleukin (IL)-2 to produce a population of HPV-specific T cells. Dividing the tumor sample, culturing the tumor fragments, obtaining T cells, testing the T cells, selecting the T cells, and expanding the numbers of selected T cells may be carried out as described herein with respect to other aspects of the invention.

The population of expanded numbers of T cells produced by the inventive methods may specifically recognize HPV-positive cells, e.g., HPV-positive cancer cells. The cells that are recognized by the T cells may be positive for any subtype of HPV such as, for example, HPV 16 or HPV 18. Alternatively or additionally, the population of T cells produced by the inventive methods may specifically recognize any HPV antigen such as, for example, any one or more of HPV 16 E6, HPV 16 E7, HPV 18 E6, and HPV 18 E7. While in some embodiments, the population of T cells may specifically recognize only one HPV antigen, in some embodiments, the population of T cells may specifically recognize more than one HPV antigen. In this regard, the population of expanded numbers of T cells may comprise multiple T cells each having different HPV specificities. For example, the population of expanded numbers of T cells may include some T cells that specifically recognize HPV 16 E6 and other T cells that specifically recognize HPV 16 E7, or the population may include some T cells that specifically recognize HPV 18 E6 and other T cells that specifically recognize HPV 18 E7. The ability of the population of expanded numbers of T cells produced by the inventive methods to specifically recognize HPV-positive cells and to specifically recognize a HPV antigen may be measured as described herein with respect to other aspects of the invention.

The population of T cells produced by the inventive methods may be useful for treating or preventing HPV-associated conditions, e.g., cancer. Accordingly, another embodiment of the invention provides a method of treating or preventing cancer in a mammal, the method comprising preparing a population of HPV-specific T cells according to any of the inventive methods described herein and administering the population of T cells to the mammal in an amount effective to treat or prevent cancer in the mammal.

Another embodiment of the invention provides a method of treating or preventing cancer in a mammal, the method comprising: dividing an HPV-positive tumor sample into multiple fragments; separately culturing the multiple fragments; obtaining T cells from the cultured multiple fragments; testing the T cells for one or both of specific autologous HPV-positive tumor recognition and HPV antigen recognition; selecting the T cells that exhibit one or both of specific autologous HPV-positive tumor recognition and HPV antigen recognition; expanding the number of selected T cells to produce a population of HPV-specific T cells for adoptive cell therapy; and administering the expanded number of T cells to the mammal in an amount effective to treat or prevent cancer in the mammal. Dividing the tumor sample, culturing the tumor fragments, obtaining T cells, testing the T cells, selecting the T cells, and expanding the numbers of selected T cells may be carried out as described herein with respect to other aspects of the invention. Another embodiment of the invention provides a method of treating or preventing a condition in a mammal, the method comprising preparing a population of HPV-specific T cells according to any of the inventive methods described herein and administering the population of T cells to the mammal in an amount effective to treat or prevent the condition in the mammal wherein the condition is cancer, HPV 16 infection, or HPV-positive premalignancy.

An embodiment of the invention comprises administering to the mammal nonmyeloablative lymphodepleting chemotherapy. The nonmyeloablative lymphodepleting chemotherapy can be any suitable such therapy, which can be administered by any suitable route. The nonmyeloablative lymphodepleting chemotherapy can comprise the administration of cyclophosphamide and fludarabine, particularly if the cancer is an HPV-positive cancer, which can be metastatic. A preferred route of administering cyclophosphamide and fludarabine is intravenously. Likewise, any suitable dose of cyclophosphamide and fludarabine can be administered. Preferably, around 60 mg/kg of cyclophosphamide is administered for two days after which around 25 mg/m$^2$ fludarabine is administered for five days, particularly if the cancer is an HPV-positive cancer. In an embodiment of the invention, the nonmyeloablative lymphodepleting chemotherapy is administered prior to administering the T cells.

An embodiment of the invention comprises, after administering the nonmyeloablative lymphodepleting chemotherapy, administering to the mammal the population of HPV-specific T cells prepared by any of the inventive methods described herein.

The T-cells can be administered by any suitable route as known in the art. Preferably, the T-cells are administered as an intra-arterial or intravenous infusion, which preferably lasts about 30 to about 60 minutes. Other examples of routes of administration include intraperitoneal, intrathecal and intralymphatic.

Likewise, any suitable dose of T-cells can be administered. Preferably, from about $1.0 \times 10^{10}$ T-cells to about $13.7 \times 10^{10}$ T-cells are administered, with an average of around $5.0 \times 10^{10}$ T-cells, particularly if the cancer is an HPV-positive cancer. Alternatively, from about $1.2 \times 10^{10}$ to about $4.3 \times 10^{10}$ T-cells are administered.

In an embodiment of the invention, any of the methods described herein may further comprise combining the population of HPV-specific T cells with a pharmaceutically acceptable carrier. The pharmaceutically acceptable carrier may be any pharmaceutically acceptable carrier that is suitable for adoptive cell therapy. For example, the pharmaceutically acceptable carrier may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

An embodiment of the invention comprises enriching cultured T cells for CD8+ T cells prior to rapid expansion of the cells. Following culture of the T cells, the T cells are depleted of CD4+ cells and enriched for CD8+ cells using, for example, a CD8 microbead separation (e.g., using a CliniMACS$^{plus}$ CD8 microbead system (Miltenyi Biotec)). Without being bound to a particular theory, it is believed that CD8+ enrichment of some T cell cultures reveals in vitro tumor recognition that may not be evident in the bulk culture, and improved in vitro recognition of tumor in other cultures. Additionally, the enriched CD8+ T cells are believed to behave more reliably and predictably in clinical scale rapid expansions than the bulk T cells.

An embodiment of the invention comprises enriching cultured T cells for CD4+ T cells prior to rapid expansion of the cells. Following culture of the T cells, the T cells are depleted of CD8+ cells and enriched for CD4+ cells using, for example, a CD4 microbead separation (e.g., using a CliniMACS$_{plus}$ CD8 microbead system (Miltenyi Biotec)).

In an embodiment, a T-cell growth factor that promotes the growth and activation of the autologous T cells is administered to the mammal either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

In an embodiment, the autologous T-cells are modified to express a T-cell growth factor that promotes the growth and activation of the autologous T-cells. Suitable T-cell growth factors include, for example, any of those described above. Suitable methods of modification are known in the art. See, for instance, Green and Sambrook, *Molecular Cloning: A Laboratory Manual*, 4$^{th}$ ed., Cold Spring Harbor Press, Cold Spring Harbor, N.Y. 2012; and Ausubel et al., *Current Protocols in Molecular Biology*, Greene Publishing Associates and John Wiley & Sons, NY, 1994. Desirably, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

The T-cell growth factor can be administered by any suitable route. If more than one T-cell growth factor is administered, they can be administered simultaneously or sequentially, in any order, and by the same route or different routes. Preferably, the T-cell growth factor, such as IL-2, is administered intravenously as a bolus injection. The dosage of the T-cell growth factor may be chosen based on patient tolerance. For example, the T-cell growth factor may be administered until one or more limiting adverse events occur. Desirably, the dosage of the T-cell growth factor, such as IL-2, is what is considered by those of ordinary skill in the art to be high. Preferably, a dose of about 720,000 IU/kg of IL-2 is administered three times daily until tolerance, particularly when the cancer is an HPV-positive cancer. Preferably, about 5 to about 15 doses of IL-2 are administered, with an average of around 9 doses.

In an embodiment, the autologous T-cells may be modified to express a T cell receptor (TCR) having antigenic specificity for an HPV antigen, e.g., any of the HPV antigens described herein. Suitable methods of modification are known in the art. See, for instance, Green and Sambrook and Ausubel, supra. For example, the T cells may be transduced to express a T cell receptor (TCR) having antigenic specificity for an HPV antigen using transduction techniques described in Heemskerk et al. *Hum Gene Ther.* 19:496-510 (2008) and Johnson et al. *Blood* 114:535-46 (2009).

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is HPV-positive cancer. The HPV-positive cancer may be, for example, HPV 16-positive or HPV 18-positive cancer. While the cancers most commonly associated with HPV infection include cancer of the uterine cervix, oropharynx, anus, anal canal, anorectum, vagina, vulva, and penis, the inventive methods may be used to treat any HPV-positive cancer, including those that occur at other anatomical areas.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. For example, the treatment or prevention provided by the inventive method can include promoting the regression of a tumor. Also, for purposes herein, "prevention" can encompass delaying the onset of the disease, or a symptom or condition thereof.

The following examples further illustrate the invention but, of course, should not be construed as in any way limiting its scope.

Example 1

This example demonstrates a method of preparing HPV-positive tumor-infiltrating lymphocytes (TIL) for adoptive cell therapy.

Patients were entered into clinical protocols and signed informed consents that were approved by the Institutional Review Board of the National Cancer Institute prior to tumor resection. Tumors were excised from patients. Tumors were tested for HPV 16 E6, HPV 16 E7, HPV 18 E6, and HPV 18 E7 expression using reverse transcriptase (RT) polymerase chain reaction (PCR) genotyping.

Multiple (24) independent cultures of HPV 16 E6 positive, HPV E7 positive, HPV 18 E6 positive, and HPV E7 positive TIL were set up using enzymatic digests and tumor fragments (1-2 mm$^3$) procured by sharp dissection. TIL from tumor digests were generated by culturing single-cell suspensions ($5 \times 10^5$/mL) obtained by overnight enzymatic digestion of tumor fragments in media containing collagenase, hyaluronidase, and DNAse. Cultures of tumor fragments and digests were initiated in 2 mL wells of complete medium (CM) and IL-2 (6000 IU/mL, Chiron Corp., Emeryville, Calif.) in a humidified 37° C. incubator with 5% $CO_2$. CM included RPMI1640 with glutamine, plus 10% human AB serum, 25 mM HEPES, 10 µg/mL gentamicin, and $5.5 \times 10^{-5}$ M 2-mercaptoethanol. Five days after initiation, one half of the media was aspirated from the wells and replaced with fresh CM and IL-2, and media was replaced every two to three days thereafter as needed. Under these conditions, lymphocytes will first lyse the adherent cells in the well, and then begin to multiply and grow.

TIL cultures achieved confluent growth of the original 2-mL well and eliminated adherent tumor cells, typically about 12-28 days after initiation. In practice, this was about $4 \times 10^6$ lymphocytes from each original tumor fragment or digest well. By pooling all the wells in a single 24 well plate, approximately $5 \times 10^7$ TIL cells would be obtained.

When cultures designated for TIL generation expanded to confluence in 2-mL wells, they were tested for HPV specific reactivity. Because the TIL were set up in large numbers (typically groups of 24 per tumor) it was not feasible to count each TIL culture individually. The TIL specificity assay measures activity per volume rather than activity per cell. Each well was mixed thoroughly, and one hundred microliters of lymphocytes (estimated $1 \times 10^5$ cells) were washed and cocultured overnight with autologous tumor digest or autologous monocyte-derived dendritic cells (DCs) pulsed with HPV 16 and HPV 18 E6 and E7 MACS PEPTIVATOR peptide pools. The peptide pools included 15-mer peptides with 11-amino-acid overlaps that covered the complete sequence of E6 or E7 (HPV 16 or HPV 18). The peptide pools were over 75% pure and low in endotoxin. IFN-γ release was then measured with enzyme-linked immunosorbent assay (ELISA). The results are shown in Table A.

TABLE A

| Patient Number | Primary Site of Cancer | HPV type | Peptide reactivity (number of tumor fragments)[1] | Tumor digest reactivity (number of tumor fragments)[2] |
|---|---|---|---|---|
| 1 | cervix | HPV-18 | E7 (22) | Yes (4) |
| 2 | tonsil | HPV-16 | E7 (5) | — |
| 3 | cervix | HPV-18 | E6 (7), E7 (19) | Yes (3) |
| 4 | cervix | HPV-16 | E6 (18), E7 (23) | No |
| 5 | cervix | HPV-16 | E6 (1) | No |
| 6 | unknown (neck) | HPV-16 | E6 (23), E7 (22) | — |
| 7 | cervix | HPV-18 | E6 (1), E7 (5) | — |
| 8 | cervix | HPV-18 | E7 (3) | — |
| 9 | cervix | HPV-18 | none | No |
| 10 | unknown (pelvic) | HPV-16 | E6 (1) | Yes (1) |
| 11 | cervix | HPV-18 | none | No |
| 12 | cervix | HPV-18 | E6, E7 | — |
| 13 | anus | HPV-16 | none | — |
| 14 | anus | HPV-16 | E6 | — |
| 15 | cervix | HPV-16 | E6, E7 | — |

[1]Defined as at least one tumor fragment with >200 pg/mL and twice background (negative control peptide pool).
[2]Defined as >200 pg/mL IFN-γ, twice background (TIL alone), and >50% blocking with W6/32 MHC class I Antibody.
"—" indicates not tested.

Rapid expansion of the numbers of HPV reactive TIL were performed using the Rapid Expansion Protocol (REP) as previously described (Dudley et al., *J. Immunother.*, 26:332-42 (2003) and Riddell et al., *J. Immunol. Methods*, 128:189-201 (1990)). Briefly, TIL cells were cultured in gas permeable, G-REX flasks with a 200 fold excess of irradiated (40 Gy) allogeneic peripheral blood mononuclear "feeder" cells in complete medium (CM) with 30 ng/mL anti-CD3 antibody and 6000 IU/mL IL-2. Half of the media was exchanged on day 5 using CM with 6000 IU/mL IL-2, and cells were split as needed thereafter. TIL expanded an average of more than 3000 fold.

Example 2

This example demonstrates the reactivity of the TIL from Patient 1.

Figure 1B:
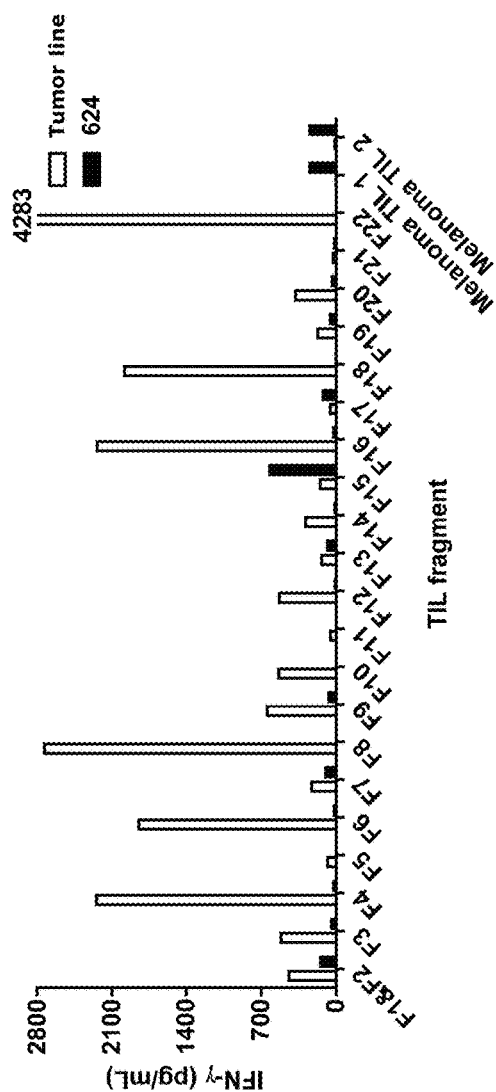
FIG. 1B is a graph showing IFN-γ (pg/mL) secreted by effector melanoma TIL or TIL generated from 22 tumor fragments (F1-F22) from Patient 1 upon co-culture with a target autologous tumor cell line (unshaded bars) or 624 cells (a melanoma cell line) (shaded bars).

TIL were generated as described in Example 1 from 22 different tumor fragments (F1-F22) from Patient 1. The TIL from Patient 1 or melanoma TIL (control) were co-cultured with dendritic cells pulsed with the HPV 18 E7 peptide pool or a gp100 peptide pool (control) and IFN-γ was measured. The results are shown in FIGS. 1A-1B. As shown in FIGS. 1A-1B, the TIL from tumor fragment 22 of Patient 1 recognized an autologous tumor line but not HPV 18 E7 peptides.

The TIL from tumor fragments F16, F17, or F22 of Patient 1 or cells given to the patient for treatment ("infusion bag") were co-cultured with autologous tumor, peripheral blood mononuclear cells (PBMC) from autologous tissue, tumor cells matched at all class I loci, HeLa cells (HLA mismatched), or CaSki cells (HLA mismatched). IFN-γ was measured. The results are shown in FIG. 2A. As shown in FIG. 2A, TIL from tumor fragments F16 and F22 showed autologous tumor recognition.

Autologous tumor cells were transfected with silencing RNA against HLA-A, HLA-B, HLA-C, or irrelevant RNA (non-targeting) and were co-cultured with TIL from Patient 1. IFN-γ was measured. The results are shown in FIG. 2B. As shown in FIG. 2B, recognition of TIL from Patient 1 was diminished by HLA-A silencing.

Effector/target cells (Patient 1 TIL/autologous tumor cells; DMF5/624 cells; or Patient 12 (P12) F15/

HPV18E6$_{121-135}$) were cultured alone or co-cultured without antibody, with anti-HLA-A2 antibody, or anti-Class II antibody. DMF5 cells are T cells transduced to express a MHC class I-restricted TCR against MART-1. The results are shown in FIG. 2C. As shown in FIG. 2C, recognition of TIL from Patient 1 was not inhibited by HLA-A*02 blocking, which suggested HLA-A*01 restricted tumor recognition. Patient 1's haplotype was HLA-A*01, HLA-A*02.

Figure 3:
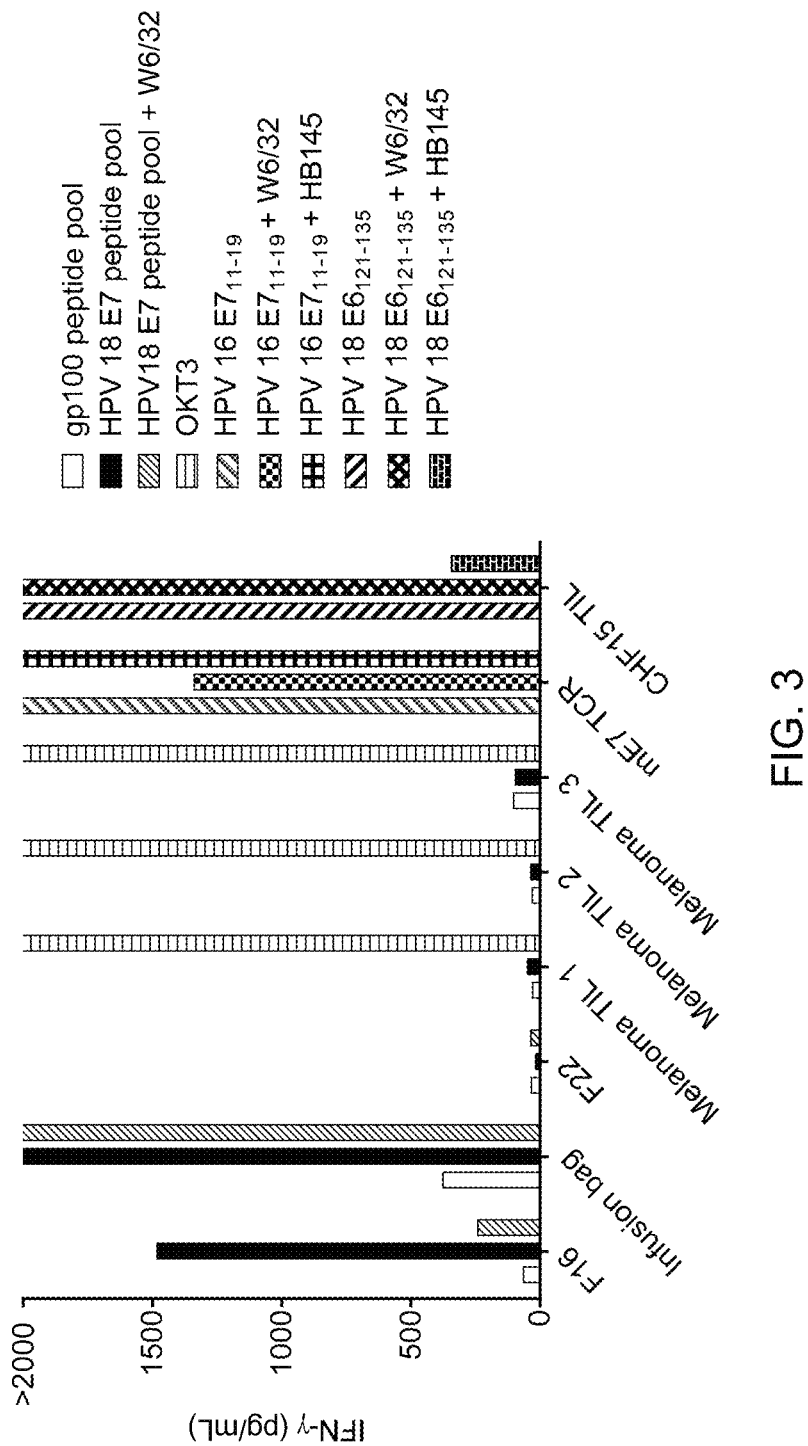
FIG. 3 is a graph showing IFN-γ (pg/mL) secreted by effector TIL from tumor fragment F16 or F22 of Patient 1; cells given to the patient for treatment ("infusion bag"); melanoma TIL 1, 2, or 3 (TIL cultured from melanoma tumors); mE7 TCR (T cells transduced to express a TCR against HPV 16 E7$_{11-19}$); or F15 TIL (TIL from another patient that were reactive against HPV 18 E6$_{121-135}$, class II-restricted, and therefore blockable with HB145) upon co-culture with a gp100 peptide pool (white bars), OKT3 antibody (horizontal striped bars), or dendritic cells (DCs) pulsed with an HPV 18 E7 peptide pool (black bars), HPV 18 E7 peptide pool and W6/32 (thin forward slash hatched bars), HPV 16 E7$_{11-19}$ (thick forward slash hatched bars), HPV 16 E7$_{11-19}$ and W6/32 (checkered bars), HPV 16 E7$_{11-19}$ and HB145 (perpendicular crossed bars), HPV 18 E6$_{121-135}$ (back slash hatched bars), HPV 18 E6$_{121-135}$ and W6/32 (crossed bars), or HPV 18 E6$_{121-135}$ and HB 145 (bars with white-outlined black rectangles).

TIL from tumor fragment F16 or F22 of Patient 1; cells given to the patient for treatment ("infusion bag"); melanoma TIL 1, 2, or 3 (TIL cultured from melanoma tumors); mE7 TCR (T cells from PBMC that were transduced to express a TCR against HPV 16 E7$_{11-19}$); or F15 TIL (TIL from another patient that were reactive against HPV 18 E6$_{121-135}$, class II-restricted, and therefore blockable with HB145) were co-cultured with a gp100 peptide pool, OKT3 antibody, or DCs pulsed with an HPV 18 E7 peptide pool, HPV 18 E7 peptide pool and W6/32, HPV 16 E7$_{11-19}$, HPV 16 E7$_{11-19}$ and W6/32, HPV 16 E7$_{11-19}$ and HB145, HPV 18 E6$_{121-135}$, HPV 18 E6$_{121-135}$ and W6/32, or HPV 18 E6$_{121-135}$ and HB 145. The results are shown in FIG. 3. As shown in FIG. 3, TIL from tumor fragment F16 of Patient 1 showed class I restricted recognition of HPV 18 E7 peptides.

Example 3

This example demonstrates the cloning of TIL from tumor fragment 16 of Patient 1 to isolate HPV 18 E7 reactive CD8 positive T cells.

Figure 4A:
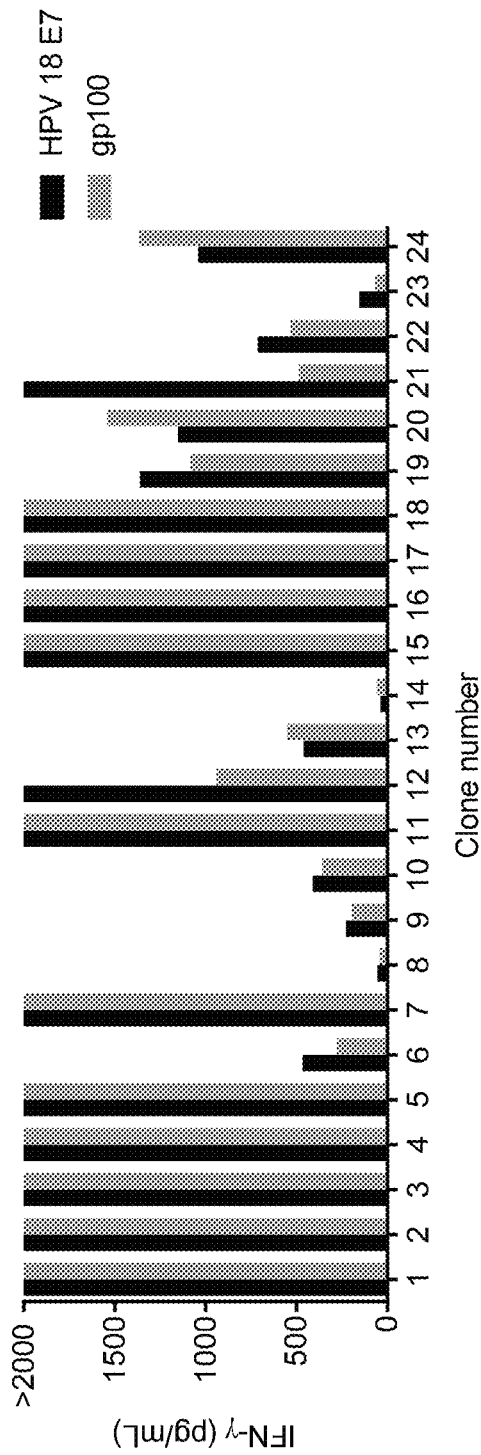
FIGS. 4A and 4B are graphs showing IFN-γ (pg/mL) secreted by effector TIL clones 1-24 (A) or clones 24-48 (B) that were cloned from the F16 tumor fragment from Patient 1 upon co-culture with a gp100 peptide pool (grey bars) or an HPV 18 E7 peptide pool (black bars).
Figure 4B:
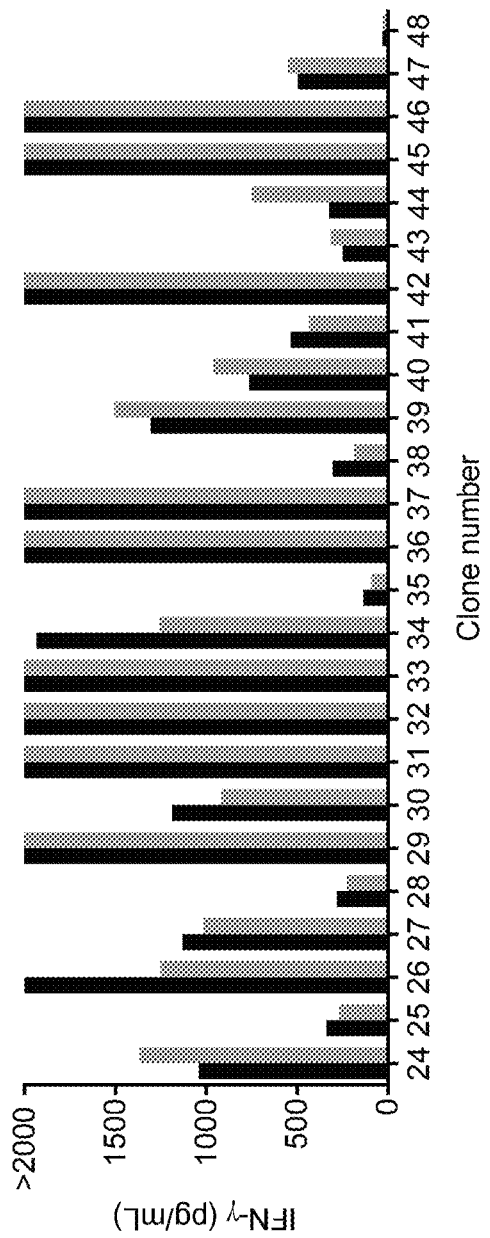

DCs were loaded with HPV 18 E7 and co-cultured with TIL from tumor fragment 16 (F16) of Patient 1. The TIL were sorted for 4-1BB positive cells using fluorescence activated cell sorting (FACS). The sorted cells were cultured in 96-well plates with two cells per well. The clones were screened for tumor reactivity against a gp100 peptide pool or a HPV 18 E7 peptide pool. The results are shown in FIGS. 4A and 4B. As shown in FIGS. 4A and 4B, CD8 positive T cell cloning from tumor fragment F16 using 4-1BB-based FACS sorting resulted in the isolation of two clones (12 and 21) with E7 peptide pool reactivity.

Example 4

This example demonstrates the reactivity of the TIL generated in Example 1 from Patient 12.

Figure 5:
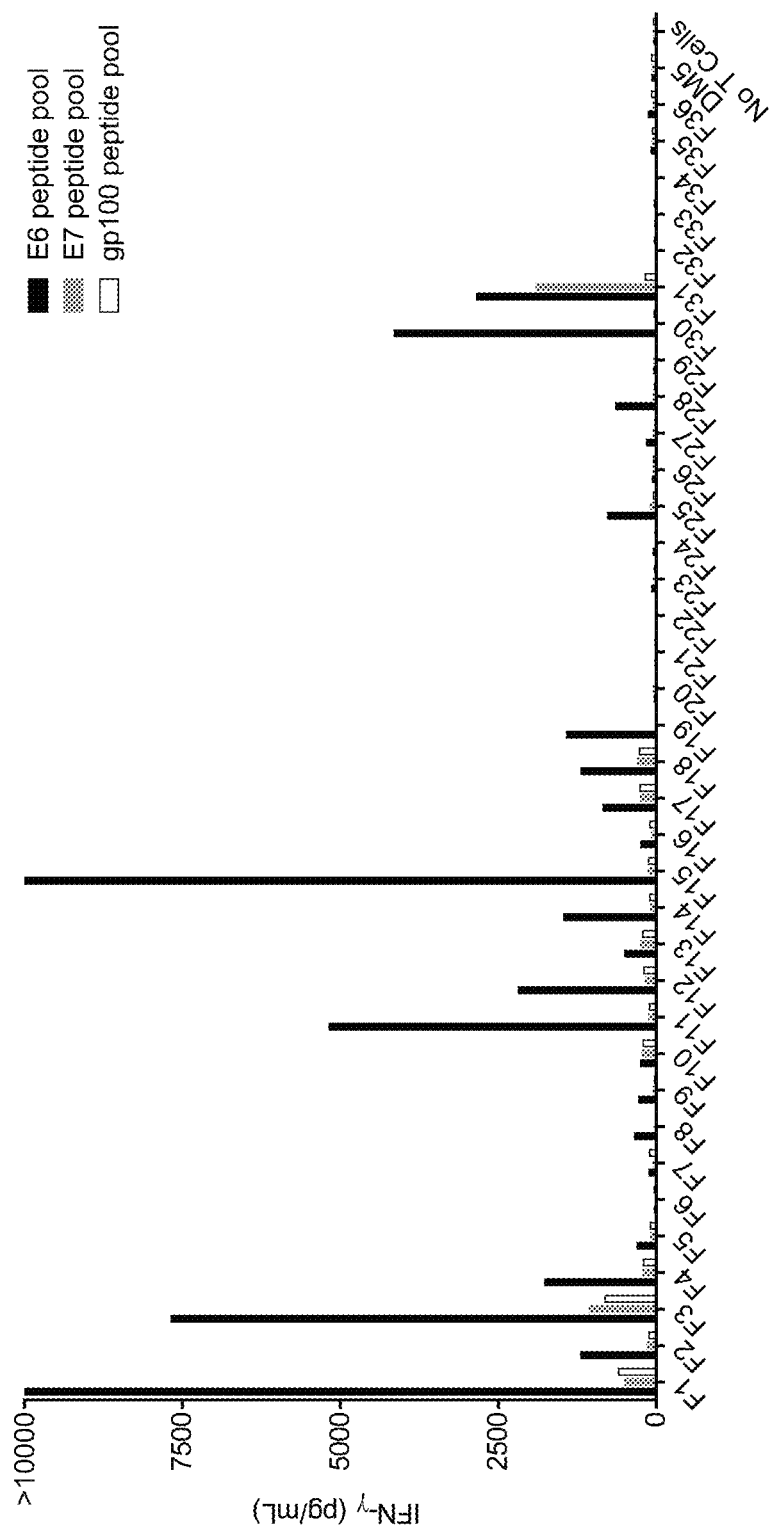
FIG. 5 is a graph showing IFN-γ (pg/mL) secreted by effector TIL from 36 different tumor fragments (F1-F36) from Patient 12 or melanoma TIL (DM5) (control) upon co-culture with dendritic cells pulsed with the HPV 18 E6 peptide pool (black bars), the HPV 18 E7 peptide pool (grey bars) or a gp100 peptide pool (control).

TIL were generated as described in Example 1 from 36 different tumor fragments (F1-F36) from Patient 12. The TIL from Patient 12 or melanoma TIL (control) were co-cultured with dendritic cells pulsed with the HPV 18 E6 peptide pool, the HPV 18 E7 peptide pool or a gp100 peptide pool (control) and IFN-γ was measured. The results are shown in FIG. 5. As shown in FIG. 5, the TIL from the F1 and F15 tumor fragments from Patient 12 showed the highest levels of IFN-γ production.

Figure 6:
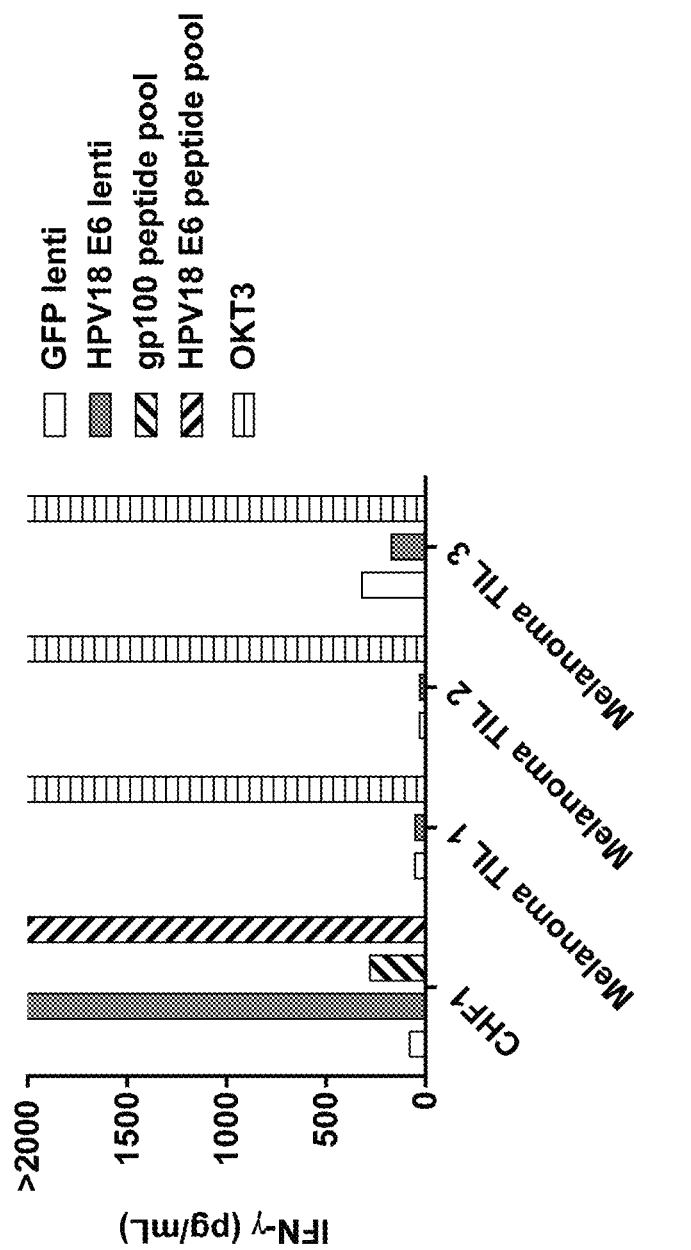
FIG. 6 is a graph showing IFN-γ (pg/mL) secreted by effector TIL generated from tumor fragment F1 of Patient 12, or melanoma TIL 1, 2, or 3, upon co-culture with DCs that were transduced with a lentiviral vector encoding green fluorescent protein (GFP) (white bars) or HPV 18 E6 (grey bars) or pulsed with a gp100 peptide pool (forward slash hatched bars) or a HPV 18 E6 peptide pool (back slash hatched bars). Horizontal striped bars indicate TIL cultured with OKT3 antibody.

Autologous DCs were transduced with an HPV 18 E6 lentiviral vector or a green fluorescent protein (GFP) lentiviral vector. Other autologous cells were pulsed with a gp100 peptide pool or a HPV 18 E6 peptide pool. Transduced cells were co-cultured with TIL from tumor fragment F1 of Patient 12, or melanoma TIL 1, 2, or 3. The results are shown in FIG. 6. As shown in FIG. 6, TIL generated from tumor fragment F1 of Patient 12 recognized DCs transduced with HPV 18 E6, suggesting that the TIL target a naturally processed and presented antigen.

Example 5

This example demonstrates the reactivity of TIL clones from tumor fragments 1 and 15 of Patient 12 to isolate HPV 18 E6 reactive CD8 positive T cells.

DCs were loaded with HPV 18 E6 and co-cultured with TIL from tumor fragments 1 and 15 of Patient 12. The TIL were sorted for 4-1BB positive cells using FACS. Cells were further sorted into CD4 positive and CD8 positive populations. The sorted cells were cultured in 96-well plates with two cells per well. The clones were screened for tumor reactivity against a HPV 18 E6 peptide pool. Out of 480 wells of CD4 positive cells from F1, 14 grew and 2 were reactive. Out of 912 wells of CD8 positive cells from F1, 33 grew and none were reactive. Out of 470 wells of CD4 positive cells from F15, 163 grew and 32 were reactive. Out of 960 wells of CD8 positive cells from F15, 41 grew and none were reactive.

The CD4 sorted cells were also tested for reactivity as measured by tumor necrosis factor (TNF) α secretion upon co-culture with a HPV 18 E6 peptide pool (a pool spanning the entire E6 protein), no peptide, subpools of the HPV 18 E6 protein, or peptides 30-37 of the HPV 18 E6 peptide pool. Each subpool contained a portion of the initial peptide pool. The results are shown in FIGS. 7A-7C. As shown in FIGS. 7A-7C, clones 3, 12, and 20 of tumor fragment F1 from Patient 12 were reactive against HPV 18 E6. The CD4 positive T cell clones that were generated recognized two sequential 15-mers with an 11 amino acid overlap. The peptides shared the epitope HPV 18 E6125-135.

Example 6

This example demonstrates that the clones generated from the F15 tumor fragment of Patient 12 recognize HPV 18 E6$_{121-135}$ in an HLA-DRB1*15 restricted manner.

Clones 3, 12, and 20 were co-cultured with donor PBMC with the haplotypes set forth in Table B. The donor PBMC were pulsed with HPV 18 E6$_{121-135}$.

TABLE B

| | HLA-DR | | HLA-DQ | | HLA-DP | |
|---|---|---|---|---|---|---|
| Donor 1 | 13:02 | 15:01 | 06 | 06 | 04:02 | 03:01 |
| Donor 2 | 03:01 | 04:01 | 02 | 03:02 | 04:02 | 02:01 |
| Donor 3 | 13:01 | 15 | 06 | 06 | 02:01 | 03:01 |
| Donor 4 | 03 | 07:01 | 02:01 | 02:02 | 04:01 | 01:01 |
| Donor 5 | 01:02 | 14 | 05:01 | 05:03 | 04:01 | 0501 |
| Donor 6 | 01:01 | 13:02 | 05:01 | 06 | 5:02 | 9:01 |
| Patient 12 | 03 | 15:01 | 02 | 06:02 | 04:01 | 09 |

TNFα secretion was measured. The results are shown in FIGS. 8A-8C. As shown in FIGS. 8A-8C, the clones generated from the F15 fragment of Patient 12 recognized HPV 18 E6$_{121-135}$ pulsed onto PBMC that were matched at both HLA-DRB1*15 and HLA-DQB1*06, but not PBMC that were matched at only HLA-DQB1*06, suggesting HLA-DRB1*15 restriction. The phenotypic allele frequency of HLA-DRB1*15 is 25 percent.

Figure 9A:
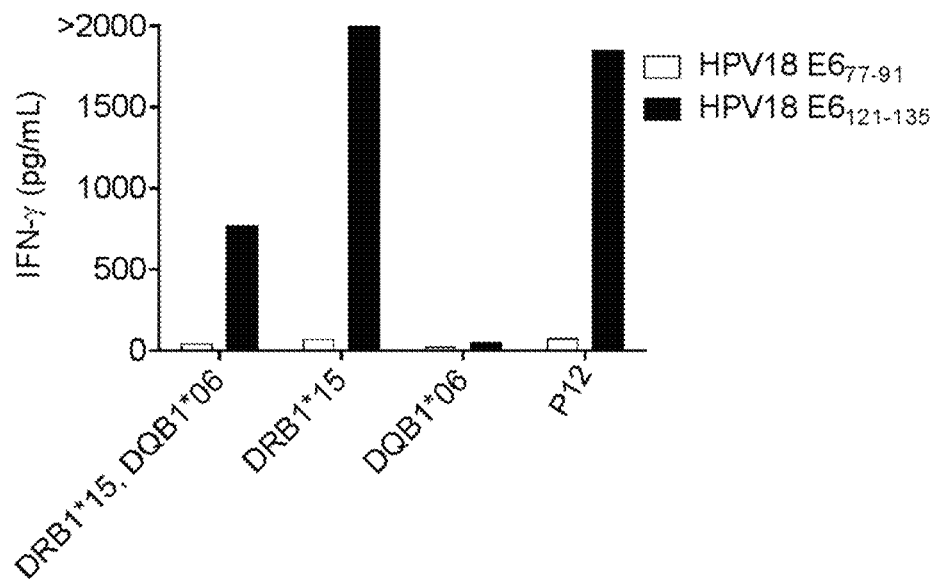
FIG. 9A is a graph showing IFN-γ (pg/mL) secreted by clone 3 of tumor fragment F15 of Patient 12 upon co-culture with autologous PBMC (P12) or DRB1*15, DQB1*06 donor PBMC, DRB1*15 donor PBMC, or DQB1*06 donor PBMC pulsed with HPV 18 E6$_{77-91}$ (unshaded bars) or HPV 18 E6$_{121-135}$ peptide (shaded bars).

The TIL from clone 3 of tumor fragment F15 of Patient 12 were co-cultured with autologous PBMC or donor PBMC pulsed with HPV 18 E6$_{77-91}$ or HPV 18 E6$_{121-135}$. The results are shown in FIG. 9A. As shown in FIG. 9A, the TIL from clone 3 of tumor fragment F15 of Patient 12 recognized PBMC matched only at DRB1*15 but not at only DRB1*06.

Figure 9B:
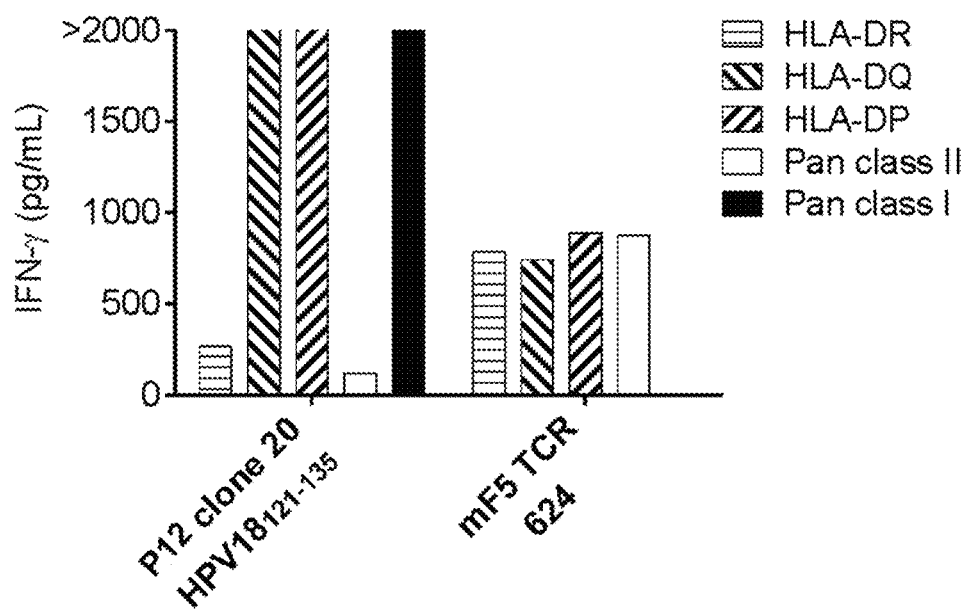
FIG. 9B is a graph showing IFN-γ (pg/mL) secreted by clone 20 of tumor fragment F15 of Patient 12 upon co-culture with PBMC pulsed with HPV 18 E6$_{121-135}$ peptide or mF5 T cells (transduced to express anti-MART-1 TCR) co-cultured with 624 cells with antibodies against HLA-DR (horizontal striped bars), HLA-DQ (back slash hatched bars), HLA-DP (forward slash hatched bars), pan-class I antibodies (black bars), or pan-class II antibodies (white bars).

The TIL from clone 20 of tumor fragment F15 of Patient 12 were co-cultured with HPV 18 E6$_{121-135}$ in the presence of antibodies against HLA-DR, HLA-DQ, HLA-DP, pan-class I antibodies, or pan-class II antibodies. Pan-class I and II antibodies block T cell binding to MHC Class I or Class II molecules, respectively. The results are shown in FIG. 9B. As shown in FIG. 9B, the recognition of cognate peptide by TIL from clone 20 of tumor fragment F15 of Patient 12 was inhibited by blocking antibodies against HLA-DR. As shown in FIGS. 9A and 9B, the TIL from tumor fragment F15 of Patient 12 recognize HPV 18 $E6_{121-135}$ in a DRB1*15 restricted manner.

Example 7

This example demonstrates the reactivity of TIL from Patients 4 and 8.

Figure 10:
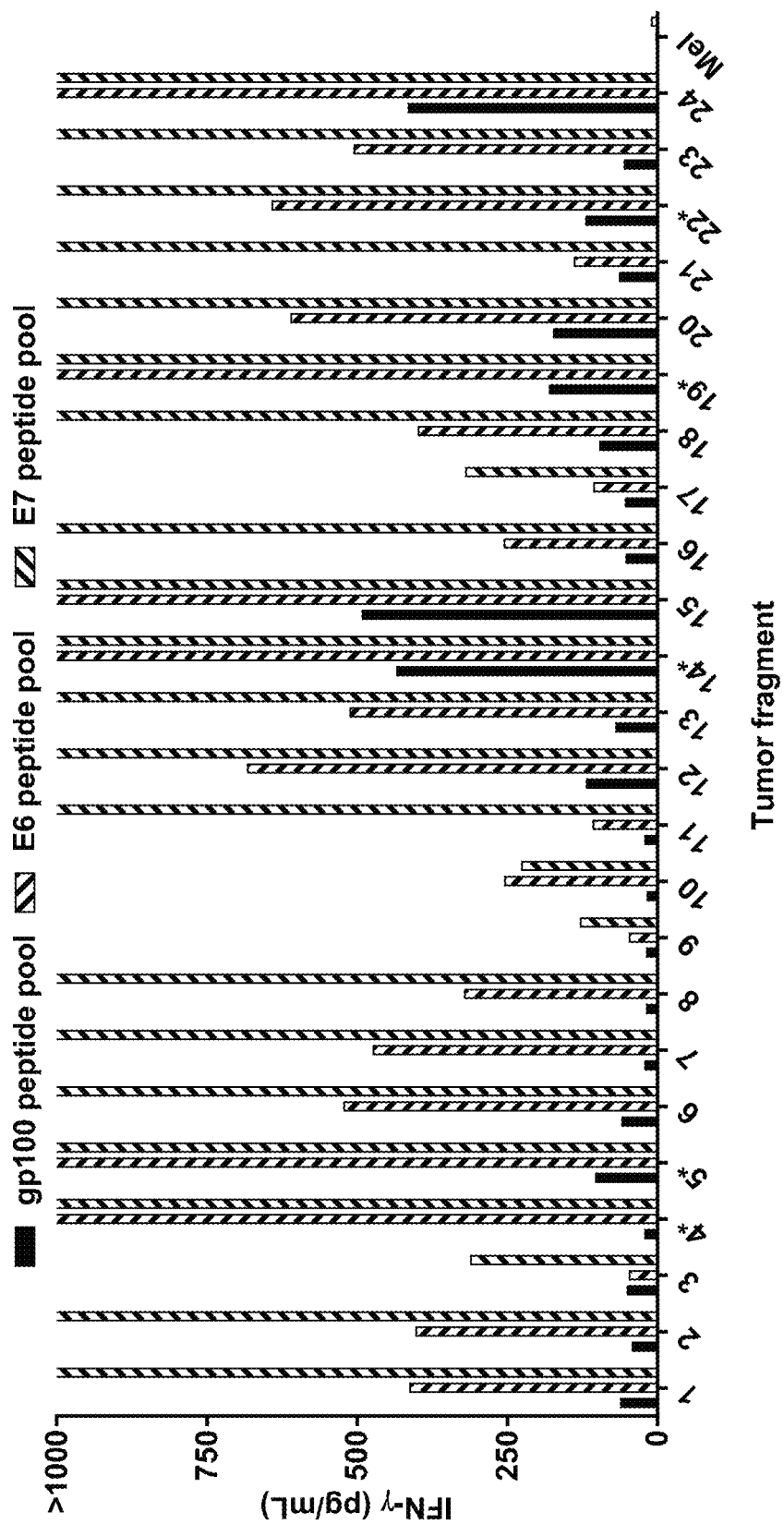
FIG. 10 is a graph showing IFN-γ (pg/mL) secreted by effector TIL from 24 different tumor fragments (F1-F24) from Patient 4 or melanoma TIL (control) upon co-culture with dendritic cells pulsed with the HPV 16 E6 peptide pool (back slash hatched bars), the HPV 16 E7 peptide pool (forward slash hatched bars) or a gp100 peptide pool (control) (black bars). Asterisk (*) indicates TIL infused into patient.

TIL were generated as described in Example 1 from 24 different tumor fragments (F1-F24) from Patient 4 or Patient 8. The TIL from Patient 4 or melanoma TIL (control) were co-cultured with autologous DCs pulsed with the HPV 16 E6 peptide pool, the HPV 16 E7 peptide pool or a gp100 peptide pool (control) and IFN-γ was measured. The results are shown in FIG. 10. As shown in FIG. 10, the TIL from F4, F5, F14, F19, and F22 tumor fragments were among those tumor fragments that showed reactivity against autologous DCs pulsed with HPV 16 E6 and E7 peptide pools.

Figure 13:
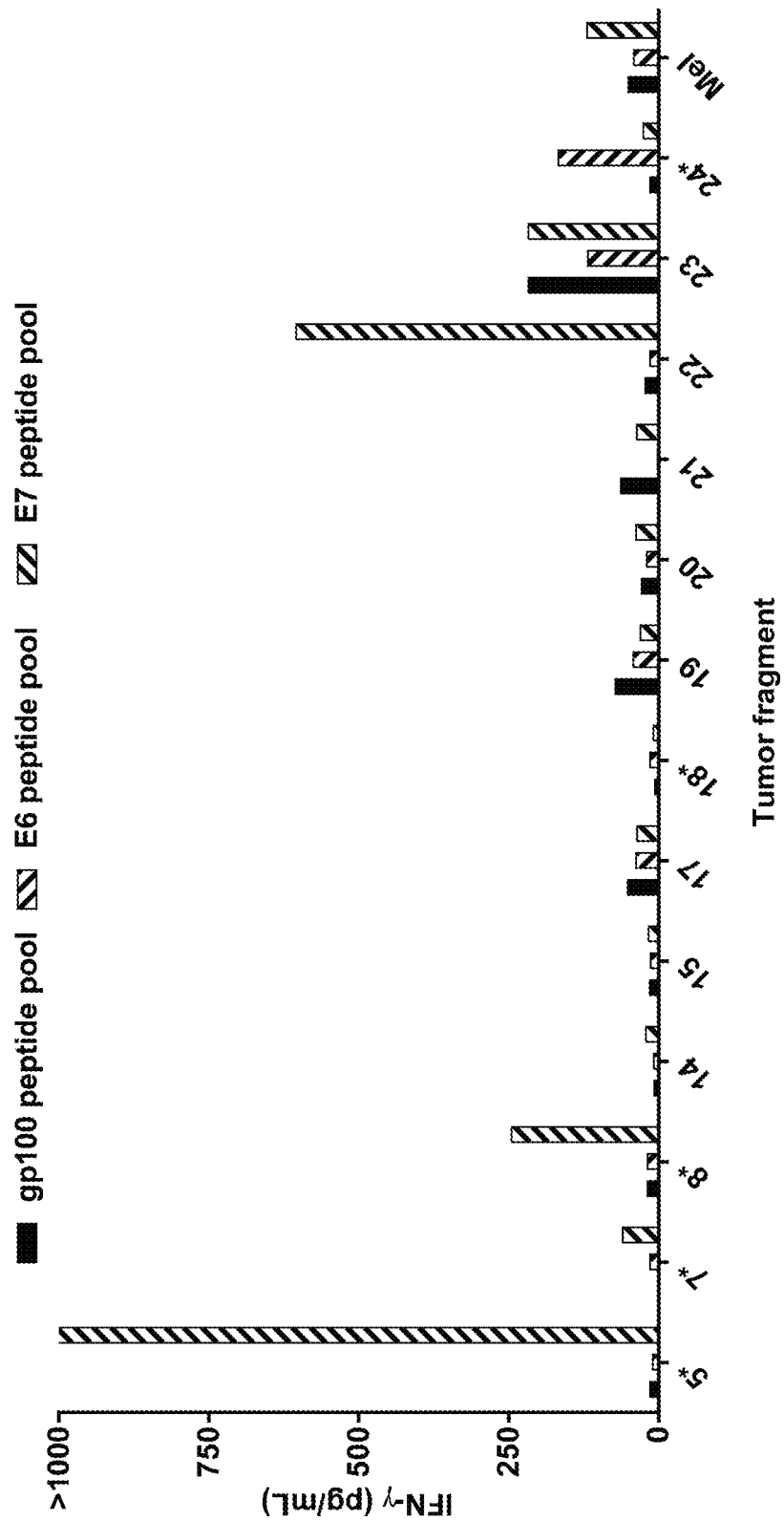
FIG. 13 is a graph showing IFN-γ (pg/mL) secreted by effector TIL from 24 different tumor fragments from Patient 8 or melanoma TIL (control) upon co-culture with dendritic cells pulsed with the HPV 18 E6 peptide pool (back slash hatched bars), the HPV 18 E7 peptide pool (forward slash hatched bars) or a gp100 peptide pool (control) (black bars). Asterisk (*) indicates TIL infused into patient.

The TIL from Patient 8 or melanoma TIL (control) were co-cultured with autologous DCs pulsed with the HPV 18 E6 peptide pool, the HPV 18 E7 peptide pool or a gp100 peptide pool (control) and IFN-γ was measured. The results are shown in FIG. 13. As shown in FIG. 13, TIL were generated that showed reactivity against autologous DCs pulsed with the HPV 18 E7 peptide pool.

Example 8

This example demonstrates the cloning of TIL from tumor fragments of Patient 4 to isolate HPV reactive CD4 and CD8 positive T cells.

DCs were loaded with HPV 16 E6 or HPV 16 E7 and co-cultured with TIL from tumor fragments of Patient 4. The HPV 16 E6 and HPV 16 E7 reactive TIL were separately sorted for 4-1BB positive cells using FACS. The numbers of cells were expanded as described in Example 1. Cells were further sorted into 4-1BB positive cells by FACS. The sorted cells were cultured in 96-well plates with two cells per well. Cells were further sorted into CD4 positive and CD8 positive populations. The clones were screened for tumor reactivity against a HPV 16 E6 or E7 peptide pool.

The results are shown in FIGS. 11A-11D. As shown in FIGS. 11A-11D, CD8 positive and CD4 positive T cell clones with reactivity against HPV 16 E6 and E7 were generated.

Example 9

This example demonstrates that adoptive cell therapy using anti-HPV T cells treats cancer.

Inclusion Criteria for the study included (1) recurrent/refractory or metastatic cervical cancer or high-risk HPV-positive cancer from any site and (2) prior chemotherapy with platinum, including chemoradiation.

Tumors were resected from patients. TIL were obtained from the tumor, grown, the numbers of TIL were expanded, and the expanded numbers of TIL were screened for HPV reactivity as described in Example 1.

Patients received a non-myeloablative, lymphodepleting preparative regimen of cyclophosphamide (60 mg/kg/day) intravenously (IV) on days −7 and −6 and fludarabine (25 mg/m2/day) IV on days −5 through −1.

TIL were intravenously administered to the patients on Day 0. A high dose of aldeskeukin (interleukin (IL)-2) (720,000 IU/kg) was intravenously administered to the patients on Days 0 through 4.

Patients underwent complete evaluation of tumor 4 to 6 weeks after the completion of the initial treatment regimen (defined as the last day of aldesleukin administration). If the patient had stable disease or tumor shrinkage, repeat complete evaluations were performed monthly for approximately 3-4 months, and then every 3-4 months until off study criteria are met. All measurable lesions up to a maximum of 10 lesions representative of all involved organs were identified as target lesions and recorded and measured at baseline. All other lesions (or sites of disease) were identified as non-target lesions and were also recorded at baseline. Lesions were evaluated according to the Response Evaluation Criteria in Solid Tumors (RECIST) guideline (version 1.0) as set forth in Table C (target lesions) and Table D (non-target lesions).

TABLE C

| | |
|---|---|
| Complete Response (CR) | Disappearance of all target lesions |
| Partial Response (PR) | At least a 30% decrease in the sum of the longest diameter (LD) of target lesions taking as reference the baseline sum LD. |
| Progression (PD) | At least a 20% increase in the sum of LD of target lesions taking as reference the smallest sum LD recorded since the treatment started or the appearance of one or more new lesions. |
| Stable Disease (SD) | Neither sufficient shrinkage to qualify for PR nor sufficient increase to qualify for PD taking as references the smallest sum LD. |

TABLE D

| | |
|---|---|
| Complete Response (CR) | Disappearance of all non-target lesions and normalization of tumor marker level |
| Non-Complete Response | Persistence of one or more non-target lesions |
| Progression (PD) | Appearance of one or more new lesions. Unequivocal progression of existing non-target lesions |

Eleven patients were treated. The results are summarized in Table E.

TABLE E

| Patient | Gender | Age | Primary site | Histology | Disease sites | Prior systemic therapy | TIL site | Cells (×10$^9$) | IL-2 doses | Response (duration in months)* |
|---|---|---|---|---|---|---|---|---|---|---|
| 1 | F | 30 | Cervix | Adeno-squamous | Lungs, hilum, retroperitoneal, iliac, vaginal cuff | Cisplatin | Lung | 101 | 7 | NR |
| 2 | M | 54 | Tonsil | Squamous | Neck, soft tissue | Docetaxel, cisplatin, 5-Fluorouracil (FU), cetuximab | Neck soft tissue | 89 | 1 | NR |

TABLE E-continued

| Patient | Gender | Age | Primary site | Histology | Disease sites | Prior systemic therapy | TIL site | Cells (×10⁹) | IL-2 doses | Response (duration in months)* |
|---|---|---|---|---|---|---|---|---|---|---|
| 3 | F | 53 | Cervix | Squamous | Lungs, liver, pelvis | Cisplatin, paclitaxel, carboplatin, topotecan, ixabepilone, phase I | Lung | 126 | 3 | PR (2) |
| 4 | F | 35 | Cervix | Squamous | Mediastinum, hilum, lung | Cisplatin, gemcitabine, topotecan, paclitaxel | Paratracheal node | 152 | 2 | PR (9+) |
| 5 | F | 55 | Cervix | Squamous | Axilla, abdominal wall | Carboplatin, 5-FU, irinotecan | Axillary lymph node (LN) | | 7 | NR |
| 6 | M | 60 | Unknown (neck) | Squamous | Liver, neck, bone, chest wall, retroperitoneal, periportal | Carboplatin, cisplatin, capecitabine | Liver | 150 | 6 | NR |
| 7 | F | 44 | Cervix | Squamous | Mediastinum, supraclavicular, brain | Cisplatin | aortopulmonary (AP) window LN | 90 | 5 | NR |
| 8 | F | 37 | Cervix | Adeno | Intraperitoneal, retroperitoneal, abdominal wall. liver surface | Cisplatin | right upper quadrant (RUQ) intraperitoneal | 75 | 8 | PR (2+) |
| 9 | F | 59 | Cervix | Adeno | Abdominal wall, lung | Cisplatin, carboplatin, paclitaxel, bevacizumab | Lung | 33 | 8 | Pending |
| 10 | F | 58 | Unknown (pelvis) | Squamous | Mediastinum, hilum, lung | Cisplatin, 5-FU, carboplatin, paclitaxel, cetuximab, irinotecan | AP window LN | 32 | 2 | Pending |
| 11 | F | 31 | Cervix | Adeno-squamous | Perihepatic, pelvic | Cisplatin, paclitaxel | Pericecal intraperitoneal | | | |

NR = No response.

As shown in Table E, out of the eight patients for which results were available, adoptive cell therapy with HPV reactive TIL resulted in three objective responders (OR), all of which were partial responders (PR). Two partial responses are ongoing at two months (Patients 3 and 4) following treatment and one partial response (Patient 8) is ongoing at nine months following treatment.

Figure 12A:
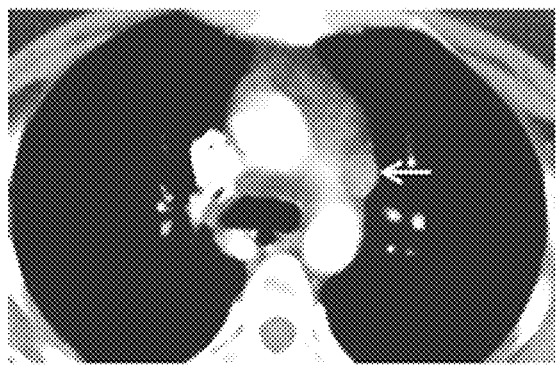
FIGS. 12A-B are computed tomography (CT) scans of the chest of Patient 4 before (A) and nine months after (B) treatment with adoptive cell therapy. The arrow in A points to a cancerous lesion in the paraaortic lymph node.
Figure 12B:
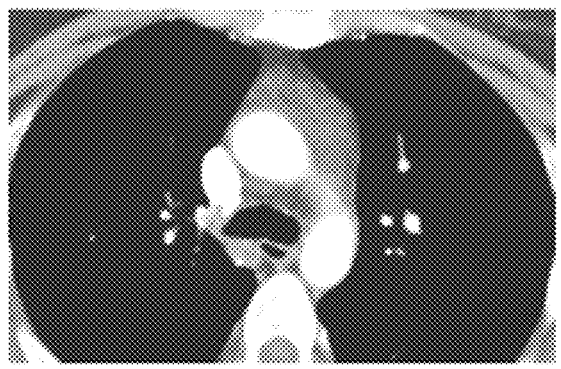
Figure 12C:
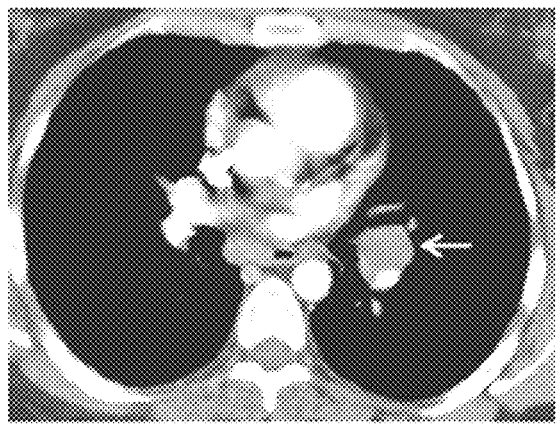
FIGS. 12C-D are CT scans of the chest of Patient 4 before (C) and nine months after (D) treatment with adoptive cell therapy. The arrow in C points to a cancerous lesion in the left lung hilar lymph node.
Figure 12D:
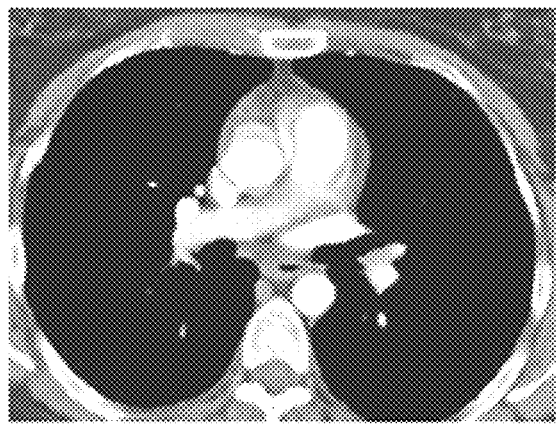
Figure 12E:
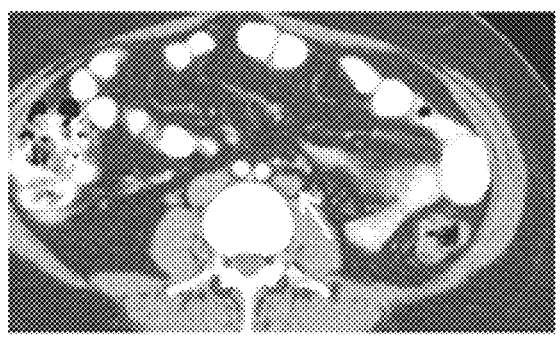
FIGS. 12E-F are CT scans of the pelvis of Patient 4 before (E) and nine months after (F) treatment with adoptive cell therapy. The arrow in E points to a cancerous lesion in the common iliac lymph node.
Figure 12F:
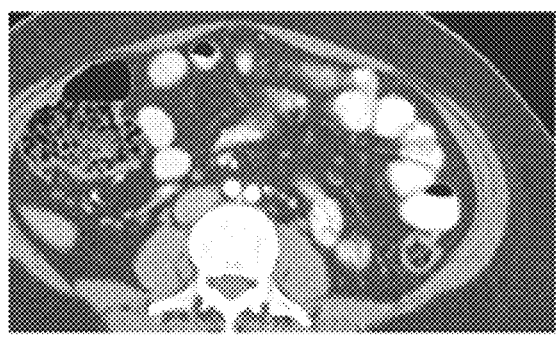

Computed tomography (CT) scans of the chest and pelvis of Patient 4 were carried out before treatment and nine months after treatment. The results are shown in FIGS. 12A-F. As shown in FIGS. 12A-B, the cancerous lesion in the paraaortic lymph node had shrunk by 100% nine months after treatment. As shown in FIGS. 12C-D, the cancerous lesion in the left lung hilar lymph node had also shrunk by 100% nine months after treatment. As shown in FIGS. 12E-F, the cancerous lesion in the common iliac lymph node had also shrunk by 100% nine months after treatment.

Figure 14A:
FIGS. 14A-B are magnetic resonance imaging (MRI) scans of the liver of Patient 8 before (A) and two months after (B) treatment with adoptive cell therapy. The arrow in A points to a cancerous liver mass.
Figure 14B:
Figure 14C:
FIGS. 14C-D are CT scans of the abdomen of Patient 8 before (C) and two months after (D) treatment with adoptive cell therapy. The arrow in C points to a cancerous lesion in the retroperitoneal lymph node.
Figure 14D:
Figure 14E:
FIGS. 14E-F are CT scans of the abdomen of Patient 8 before (E) and two months after (F) treatment with adoptive cell therapy. The arrow in E points to a cancerous abdominal wall mass.
Figure 14F:
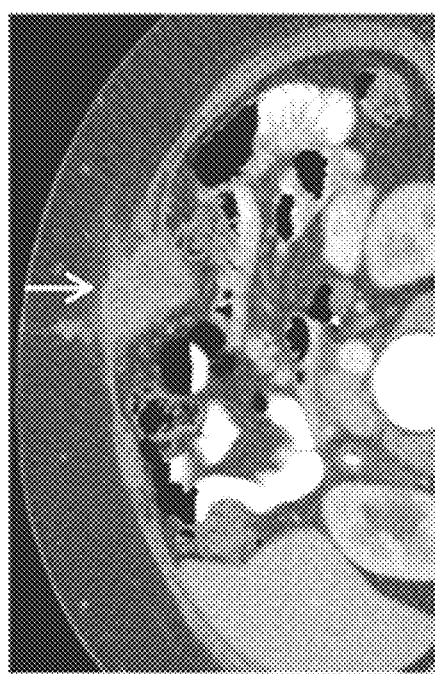
Figure 14G:
FIGS. 14G-H are CT scans of the pelvis of Patient 8 before (G) and two months after (H) treatment with adoptive cell therapy. The arrow in G points to a cancerous left pericolic mass.
Figure 14H:
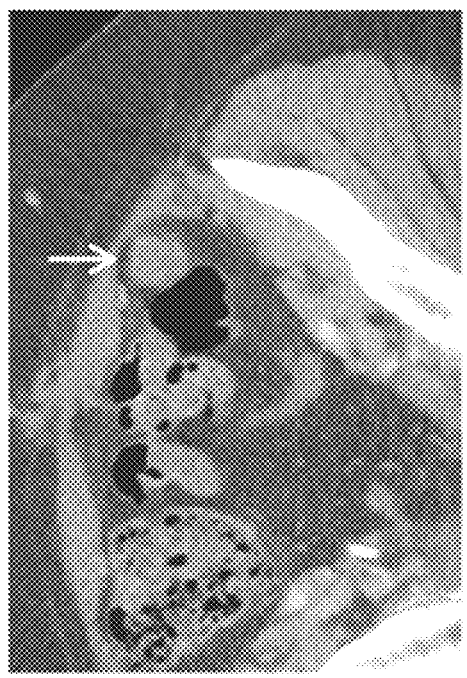

Magnetic resonance imaging (MRI) scans of the liver of Patient 8 were carried out before treatment and two months after treatment. The results are shown in FIGS. 14A-14B. As shown in FIGS. 14A-B, the cancerous mass on the liver shrunk by 100% two months after treatment. CT scans of the abdomen and pelvis of Patient 8 were also carried out before treatment and two months after treatment. The results are shown in FIGS. 14C-H. As shown in FIGS. 14C-D, the cancerous lesion in the retroperitoneal lymph node had also shrunk by 100%. As shown in FIGS. 14E-F, the cancerous mass in the abdominal wall had also shrunk by 100%. In addition, as shown in FIGS. 14G-H, the cancerous left pericolic mass shrunk dramatically.

Example 10

This example provides updated results of the clinical study described in Example 9 that were obtained nine months after the results described in Example 9 were obtained. This example demonstrates that adoptive cell therapy using anti-HPV T cells treats cancer.

Methods: A clinical trial to treat metastatic HPV+ cancers with tumor-infiltrating lymphocytes (TIL) selected for HPV E6- and E7-reactivity (HPV-TIL) was carried out as described in Example 9. HPV-TIL infusion was preceded by non-myeloablative conditioning and followed by high-dose bolus aldesleukin as described in Example 9. HPV-reactivity was assessed by ELISPOT, IFN-gamma production, and CD137 expression assays.

Results: Nine cervical cancer patients were treated on the study. They received a median of $81 \times 10^9$ T cells (range 33 to $152 \times 10^9$) as a single infusion. The infused cells possessed reactivity against high-risk HPV E6 and/or E7 in 6/8 patients. The two patients with no HPV reactivity did not respond to treatment. Three out of six patients with HPV reactivity demonstrated objective tumor responses by RECIST (1 PR and 2 CR). One patient had a 39% best response. Two patients with widespread metastases had complete tumor responses that were ongoing 18 and 11 months after treatment. One patient with a complete response had a chemotherapy-refractory HPV-16+ squamous cell carcinoma (Patient 4 of Example 9) and the other a chemoradiation-refractory HPV-18+ adenocarcinoma (Patient 8 of Example 9). Both patients demonstrated prolonged repopulation with HPV-reactive T cells following treatment. Increased frequencies of HPV-specific T cells were detectable after 13 months in one patient and 6 months in the other. Two patients with HPV-reactive TIL that did not respond to treatment did not display repopulation with HPV-reactive T cells.

Six non-cervical cancer patients were also treated on the study. One patient experienced an objective clinical response, that is, a partial response of a metastatic tonsil cancer that was ongoing four months after treatment (FIGS. 20A-J).

The results are shown in Tables F-G.

TABLE F

HPV-TIL cervical cancer cohort

| Patient | Age | Histology | HPV type | Disease sites | Prior systemic therapy | TIL site | Cells (×10$^9$) | IL-2 doses | Response (duration in months)* |
|---|---|---|---|---|---|---|---|---|---|
| 1 | 30 | Adenosquamous | HPV-18 | Lungs, hilum, retroperitoneal, iliac, vaginal cuff | Cisplatin | Lung | 101 | 7 | PD |
| 3 | 53 | Squamous | HPV-18 | Lungs, liver, pelvis | Cisplatin, paclitaxel, carboplatin, topotecan, ixabepilone, phase I | Lung | 126 | 3 | PR (3) |
| 4 | 35 | Squamous | HPV-16 | Mediastinum, hilum, lung, illiac | Cisplatin, gemcitabine, topotecan, paclitaxel | Paratracheal node | 152 | 2 | CR (18+) |
| 5 | 55 | Squamous | HPV-16 | Axilla, abdominal wall | Carboplatin, 5-FU, irinotecan | Axillary LN | 81 | 7 | PD |
| 7 | 44 | Squamous | HPV-18 | Mediastinum, supraclavicular, brain | Cisplatin | AP window LN | 90 | 5 | PD |
| 8 | 37 | Adeno | HPV-18 | Paracolic, retroperitoneal, abdominal wall, liver surface | Cisplatin | RUQ intraperitoneal | 75 | 8 | CR (11+) |
| 9 | 59 | Adeno | HPV-18 | Abdominal wall, lung | Cisplatin, carboplatin, paclitaxel, bevacizumab | Lung | 33 | 8 | PD |
| 11 | 31 | Adenosquamous | HPV-18 | Perihepatic, pelvic | Cisplatin, paclitaxel | Pericecal | 46 | 9 | PD |
| 12 | 37 | Adeno | HPV-18 | Pelvis, retropertioneum, axilla, mediastinum, lung | Carboplatin, paclitaxel, ipilimumab | Supraclavicular LN | 70 | 1 | PD |

*Measured in months from cell infusion.

TABLE G

HPV-TIL non-cervical cancer cohort

| Patient | Gender | Age | Primary site | Histology | Disease sites | Prior systemic therapy | TIL site | Cells (×10$^9$) | IL-2 doses | Response (duration in months)* |
|---|---|---|---|---|---|---|---|---|---|---|
| | | | | | Head and neck | | | | | |
| 2 | M | 54 | Tonsil | Squamous | Neck, soft tissue | Docetaxel, cisplatin, 5-FU, cetuximab | Neck soft tissue | 89 | 1 | PD |
| 6 | M | 60 | Unknown (neck) | Squamous | Liver, neck, bone, chest wall, retroperitoneum, periportal | Carboplatin, cisplatin, capecitabine | Liver | 150 | 6 | PD |
| 13 | M | 60 | Tonsil | Squamous | Lung, hilum | Docetaxel, cisplatin, bevacizumab, cetuximab, gemcitabine | Lung | 131 | 5 | PR (4+) |
| | | | | | Anal | | | | | |
| 10 | F | 58 | Unknown (pelvis with AIN) | Squamous | Mediastinum, hilum, lung | Cisplatin, 5-FU, carboplatin, paclitaxel, cetuximab, irinotecan | AP window LN | 32 | 2 | PD |
| 14 | F | 49 | Anal | Squamous | Mediastinum, retroperitoneum, pelvis | 5-FU, mitomycin, cisplatin, carboplatin, protein-bound paclitaxel | Neck LN | 69 | 3 | PD |
| 15 | F | 58 | Anal | Squamous | Liver, retroperitoneum, pelvis | 5-FU, mitomycin, cisplatin | Liver | 48 | 6 | PD |

*Measured in months from cell infusion.

These data show that HPV-TIL can mediate durable, complete regression of metastatic cervical cancer and that cellular therapy can mediate complete regression of an epithelial malignancy. These data also show that HPV-TIL can mediate regression of a metastatic tonsil cancer.

Example 11

This example further describes the complete tumor responses obtained in Example 10 with adoptive cell therapy using anti-HPV T cells.
Methods
HPV-TIL generation: Tumor-infiltrating lymphocytes (TIL) were grown from 2 mm fragments of excised tumors as described previously (Dudley et al., *J. Immunother.*, 26(4): 332-42 (2003)). After two to three weeks of lymphocyte outgrowth, the cultures were assessed for cellular composition by flow cytometry and for reactivity against HPV type-specific E6 and E7 by interferon (IFN)-gamma production assay as described in the Assessment of HPV oncoprotein reactivity section below. Flow cytometric analysis was performed with fluorescent antibodies specific for CD3, CD4, CD8, and CD56 (BD Biosciences). Cultures were selected for additional expansion based on reactivity against the HPV oncoproteins, rapid growth, high T cell purity, and high frequency of CD8+ T cells. Expansion to the cell numbers used for treatment was accomplished with a rapid expansion protocol with G-REX gas permeable flasks (Dudley et al., *J. Immunother.*, 26(4): 332-42 (2003); Jin et al., *J. Immunother.*, 35(3): 283-92 (2012)). Infusion products were certified for viable cell numbers, T cell purity (flow cytometry), potency (IFN-γ production), sterility (microbiological studies), and absence of tumor cells (cytopathology).

Patient treatments: Patients had metastatic cervical cancer and measurable disease. Prior treatment with a platinum agent in either the primary chemoradiation or metastatic setting was required. The conditioning regimen consisted of cyclophosphamide 60 mg/kg IV daily for two days followed by fludarabine 25 mg/m$^2$ IV daily for five days. Cells were administered IV over 20 to 30 minutes. Aldesleukin 720,000 IU/kg/dose IV was initiated within 24 hours of cell infusion and continued every eight hours until stopped for toxicity or for a maximum of 15 doses. Filgrastim was initiated the day after cell infusion and continued until neutrophil counts recovered.

Tumor responses: Baseline imaging studies were obtained within four weeks before initiating the conditioning regimen. Follow-up imaging was obtained six weeks after treatment, monthly for three assessments, every three months for three assessments, and then every 6 months for two assessments.

Assessment of HPV oncoprotein reactivity: HPV reactivity was determined by coculture of T cells (40,000 to 100,000 cells) with autologous immature dendritic cells (40,000 cells) loaded with 1 µM of peptide pools spanning E6, E7, gp100, or EBNA1 and BZLF1 (Miltenyi Biotec, Bergisch Gladbach, Germany). Peptide pools included 15-mer peptides overlapping by 11 amino acids. Dendritic cells were generated from the adherent fraction of peripheral blood mononuclear cells (PBMC) or from CD14+ cells isolated from PBMC using magnetic bead isolation (Miltenyi Biotec) by culturing in DMEM supplemented with 10% human serum and 1000 IU/ml GM-CSF and 500 IU/ml IL-4 for five to six days. Anti-EBV control T cells were generated before treatment by culturing PBMC with EBNA1 and BZLF1 peptide pools (10 µg/mL) in AIM-V/RPMI media supplemented with 10% human serum and 3000 IU/ml IL-2.

For IFN-γ production assays, the concentration of IFN-γ in the supernatants was determined after overnight coculture (R&D Systems (Minneapolis, Minn.) or Thermo Fisher Scientific (Waltham, Mass.)).

ELISPOT (Mabtech (Cincinnati, Ohio)) analysis was performed according to the manufacturer's instructions. Briefly, ELIIP plates (WAIPSWU from Millipore (Billerica, Mass.)) precoated with capture antibody (clone 1-D1K, Mabtech) were seeded with 10,000 effector cells and 40,000 target cells. After 16 to 18 hours of incubation, IFN-γ secretion was detected by addition of a biotinylated anti-IFN-γ antibody (7-B6-1 biotin, Mabtech) for two hours at room temperature. Following incubation with streptavidin-alkaline phosphatase (Mabtech) for one hour, substrate reagent (5-bromo-4-chloro-3'-indolyphosphate p-toluidine/nitro-blue tetrazolium chloride, Kirkegaard & Perry Laboratories, Inc. (Gaithersburg, Md.)) was added to allow spot formation. Spot formation was stopped by rinsing with tap water. Spots were counted using an IMMUNOSPOT automated reader (Cellular Technology, Ltd. (Shaker Heights, Ohio)). ELIPSOT responses against E6 or E7 were defined as positive if more than two times the negative control and greater than 10 spots/well.

CD137 upregulation assays were performed by flow cytometric analysis after 20 to 24 hour coculture (Wolff et al., *Blood*, 110(1): 201-10 (2007)). Cells were labeled with fluorescent antibodies against CD137, CD4, CD8, and CD3 (BD Biosciences, San Jose, Calif.). They were counterstained with propidium iodide (BD Pharmingen, Franklin Lakes, N.J.) prior to data acquisition with a BD FACSCANTO II cell analyzer (BD Biosciences). Data was analyzed with FLOWJO software, Mac version 10 (TreeStar, Ashland, Oreg.).

Immunohistochemistry: Immunohistochemical stainings were performed in the Laboratory of Pathology, NCI, on 4 µM sections from formalin-fixed, paraffin-embedded metastatic tumors according to standard procedures. After deparaffinization, rehydration, and antigen retrieval, tumor sections were incubated with anti-human CD4 clone 1F6 (Novocastra, Wetzlar, Germany) at a 1:80 dilution for 2 hours, anti-human CD8 clone CD8/144B (Dako Corp., Glostrup, Denmark) at a 1:50 dilution for 2 hours, or anti-human p16 clone JC8 (Santa Cruz, Dallas, Tex.) at a 1:200 dilution for 32 minutes. The CD4 stained slides were stained on an AUTOSTAINER Link 48 (Dako Corp.) and visualized with the ENVISION FLEX+ detection system (Dako Corp.). The CD8 and p16 stained slides were stained on a VENTANA Benchmark XT (Ventana Medical Systems, Tucson, Ariz.) and visualized with the ULTRAVIEW detection system (Ventana Medical Systems). Images were captured with 10× microscopy.

Determination of lymphocyte subsets from peripheral blood: Complete blood counts with manual differential determination were performed by the Clinical Center Hematology Laboratory. Lymphocyte phenotyping for T, B, and NK cells was performed by the NIH Immunology Flow Cytometry Laboratory using standardized criteria.

Real-time reverse transcription polymerase chain reaction (RT-PCR): RNA was isolated from a 2 mm fragment of fresh tumor tissue using an RNEASY kit (Qiagen, Valencia, Calif.). Reverse transcription first-strand DNA synthesis was performed using QSCRIPT cDNA supermix (Quanta BioSciences, Gaithersburg, Md.). Custom made TAQMAN primer and probe sequences (Applied Biosciences, Foster City, Calif.) were used for HPV16-E6, HPV16-E7, HPV18-E6, and HPV18-E7. Readily available glyceraldehyde-3-phosphate dehydrogenase (GAPDH) primer probe set was used to standardize oncoprotein expression levels (Hs02758991_g1, Applied Biosciences, Foster City, Calif.). RT-PCR was performed on a 7500 FAST REAL-TIME PCR System (Applied Biosciences).

Analysis of serum cytokine levels: Levels of 17 cytokines (IL-1β, IL-2, IL-4, IL-5, IL-6, IL-7, IL-8, IL-10, IL-12p70, IL-13, IL-17, granulocyte-colony stimulating factor (G-CSF), granulocyte monocyte-colony stimulating factor (GM-CSF), IFN-γ, monocyte chemotactic protein (MCP)-1, macrophage inflammatory protein (MIP)-1β, and tumor necrosis factor (TNF)-α were measured in sera from patients collected before and after treatment with HPV-TIL using BIO-PLEX Pro Human Cytokine 17-plex Assay (Bio-Rad Laboratories) according to the manufacturer's instructions. The cytokine levels were acquired by the BIO-PLEX 200 system (Bio-Rad).

Case Reports

Patient 4 was diagnosed with stage 3B poorly-differentiated, squamous cell cervical cancer fourteen months before treatment with HPV-TIL. The patient was initially treated with cisplatin, vincristine, and bleomycin followed by chemoradiotherapy with gemcitabine plus cisplatin, and brachytherapy. Two months later, metastatic cancer was detected in paratracheal (biopsy-confirmed), subcarinal, and bilateral hilar lymph nodes. She received four cycles of topotecan and paclitaxel before disease progression, and then was referred for the clinical trial described in Examples 9 and 10. HPV-TIL was prepared from a resected paratracheal lymph node. The patient received lymphocyte-depleting chemotherapy followed by a single intravenous infusion of $152 \times 10^9$ HPV-TIL and two doses of aldesleukin. Aldesleukin dosing was stopped for patient fatigue. She was discharged from the hospital after hematological recovery, 12 days after cell infusion.

Patient 8 was diagnosed with stage IB2 adenocarcinoma of the uterine cervix 17 months before treatment with HPV-TIL. Her primary tumor was treated with chemoradiation with cisplatin followed by brachytherapy. Five months later, she was noted to have a chemoradiation-refractory primary tumor (biopsy-confirmed). Salvage surgery identified paraaortic and iliac lymph node involvement and residual pelvic disease. Her cancer progressed to involve additional retroperitoneal lymph nodes and the liver surface, and she developed right hydroureteronephrosis and bilateral pulmonary emboli, which required a ureteral stent and anticoagulation therapy. The patient was then treated according to the protocol described in this Example using HPV-TIL generated from two peritoneal nodules. She received lymphocyte-depleting chemotherapy followed by $75 \times 10^9$ HPV-TIL cells and eight doses of aldesleukin. Aldesleukin dosing was stopped for hypoxia secondary to pulmonary edema, which required supplemental oxygen and resolved with diuresis. Discharge from the hospital was 11 days after cell infusion.

Complete Clinical Responses

Figure 15A:
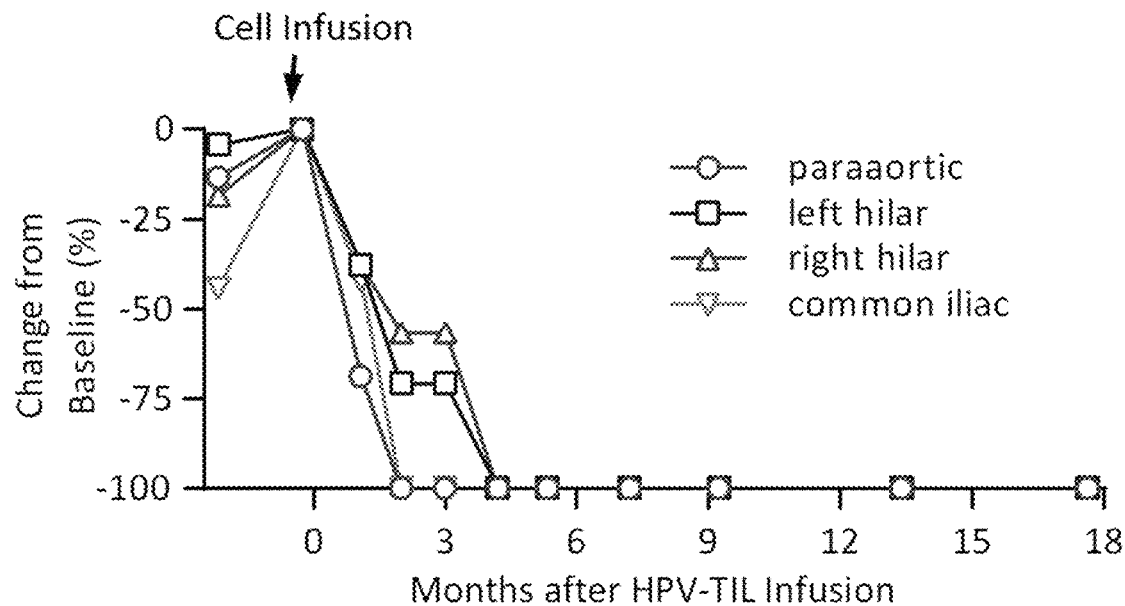
FIG. 15A is a graph showing paraaortic (circles), left hilar (squares), right hilar (Δ), and common iliac (∇) tumor size measurement (% change from baseline) of Patient 4 at time points (number of months) after HPV-TIL infusion.
Figure 15B:
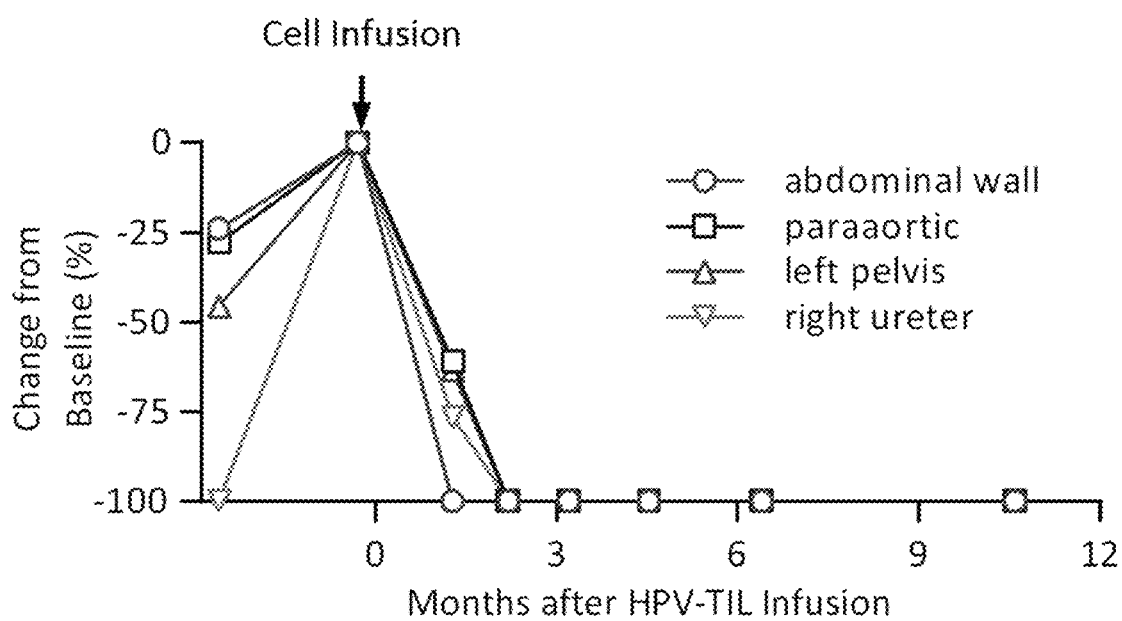
FIG. 15B is a graph showing abdominal wall (circles), paraaortic (squares), left pelvis (Δ), and right ureter (∇) tumor size measurement (% change from baseline) of Patient 8 at time points (number of months) after HPV-TIL infusion.

Both patients had disseminated progressive disease before treatment (FIG. 12A-F; FIG. 14A-H; FIG. 15 A-B; FIG. 16A-D; FIG. 21A-H; and FIG. 22A-H). Patient 4 had metastatic tumors involving a paraaortic mediastinal lymph node, bilateral lung hila, subcarinal lymph nodes, and iliac lymph nodes (FIG. 15 A; FIG. 12A-F; and FIG. 21A-H). Patient 8 had metastatic cancer involving at least seven sites: two tumors on the liver surface, paraaortic and aortocaval lymph nodes, the abdominal wall, a pericolic mass in the left pelvis, and a nodule obstructing the right ureter (FIG. 15 B; FIG. 14A-H; FIG. 16A-D; and FIG. 22A-H). Each patient was treated with a single infusion of T cells, which resulted in tumor regression that occurred over months (FIG. 15A-B). Both patients experienced objective complete tumor responses, which were ongoing 18 and 11 months after treatment (FIG. 21A-H (Patient 4) and FIG. 22A-H (Patient 8). A previously placed ureteral stent was removed from Patient 8 following regression of the tumor obstructing her right ureter (FIGS. 22 G and H). Neither patient received additional therapy. Both patients have returned to full-time employment.

Toxicity of HPV-TIL

Figure 17A:
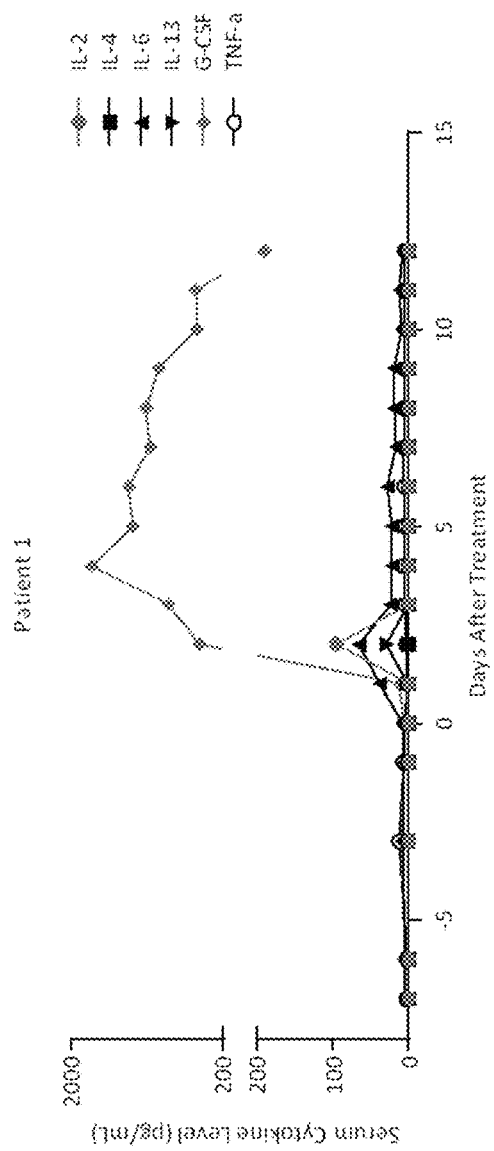
FIG. 17A is a graph showing the serum cytokine level (pg/ml) measured in Patient 4 at time points (number of days) after treatment. Cytokines measured include interleukin (IL)-2 (closed circles), IL-4 (squares), IL-6 (▲), IL-13 (▼), granulocyte colony-stimulating factor (G-CSF) (diamonds), and tumor necrosis factor alpha (TNF-a) (open circles). Cytokines that were administered to the patient are underlined.
Figure 17B:
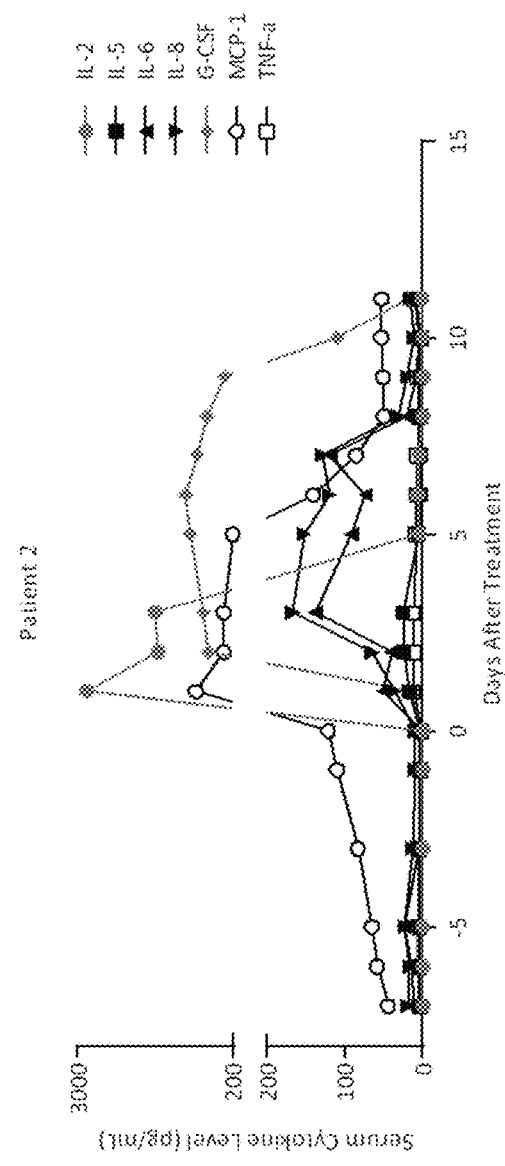
FIG. 17B is a graph showing the serum cytokine level (pg/ml) measured in Patient 8 at number of days after treatment. Cytokines measured include IL-2 (closed circles), IL-5 (closed squares), IL-6 (▲), IL-8 (▼), G-CSF (diamonds), monocyte chemoattractant protein-1 (MCP-1) (open circles), and TNF-a (open squares). Cytokines that were administered to the patient are underlined.

There were no acute toxicities related to cell infusion. No autoimmune adverse events occurred. Both patients displayed transient serum cytokine elevations (FIG. 17A-B) that were associated with fevers, but neither patient developed severe cytokine release syndrome. The levels of cytokines in cryopreserved serum were determined. Testing was for the following cytokines: IL-1β, IL-2, IL-4, IL-5, IL-6, IL-7, IL-8, IL-10, IL-12(p70), IL-13, IL-17, G-CSF, Granulocyte macrophage colony-stimulating factor (GM-CSF), IFN-γ, MCP-1, Macrophage inflammatory protein 1 beta (MIP-1β), and TNF-α. Cytokines with levels greater than twofold baseline on two consecutive measurements are displayed. Aldesleukin was dosed every eight hours after cell infusion (Patient 4 received two doses and Patient 8 received eight doses). GCSF was administered daily beginning the day after cell infusion and continued until neutrophil counts recovered (Patient 4 received 11 doses and Patient 8 received nine doses).

Aldesleukin was dosed to tolerance by protocol design, stopping for fatigue in Patient 4 and dyspnea in Patient 8. Grade 3 and grade 4 adverse events are listed in Table H. The most common toxicities were hematological and the expected effects of the lymphocyte-depleting conditioning regimen (cyclophosphamide and fludarabine).

TABLE H

| Toxicity | Patient 4 | Patient 8 |
| --- | --- | --- |
| Anemia | X | X |
| Neutropenia | X | X |
| Lymphopenia | X | X |
| Leukopenia | X | X |
| Thrombocytopenia | X | X |
| Febrile Neutropenia | X | X |
| Infection | | X |
| Fatigue | X | |
| Nausea/Vomiting | X | X |
| Syncope† | | X |
| Lower gastrointestinal (GI) hemorrhage* | | X |
| Hematuria* | | X |
| Hypophosphatemia | X | |

†A single episode of unknown etiology 15 days after treatment.
*Associated with radiation cystitis and colitis.

Tumor Antigen Expression and T Cell Infiltration

Metastatic tumors excised for the generation of HPV-TIL were a squamous cell carcinoma from Patient 4 and an adenocarcinoma from Patient 8. The malignant cells expressed p16INK4A, a sensitive indicator of high-risk HPV-infection. The HPV type and the expression levels of E6 and E7, the target antigens of HPV-TIL, were determined for each patient's tumor by real-time reverse transcription polymerase chain reaction (RT-PCR). Patient 4 had a HPV-16+ cancer and Patient 8 had a HPV-18+ cancer. The T cell infiltrate in tumors from both patients showed a mixed composition with predominantly CD8+ cells in Patient 4 and CD4+ cells in Patient 8. Both CD4+ and CD8+ T cells grew from the excised tumors. The infused HPV-TIL were composed of 19% CD4+ and 79% CD8+ T cells for Patient 4, and 15% CD4+ and 87% CD8+ T cells for Patient 8.

HPV Oncoprotein Targeting by HPV-TIL

Figure 18A:
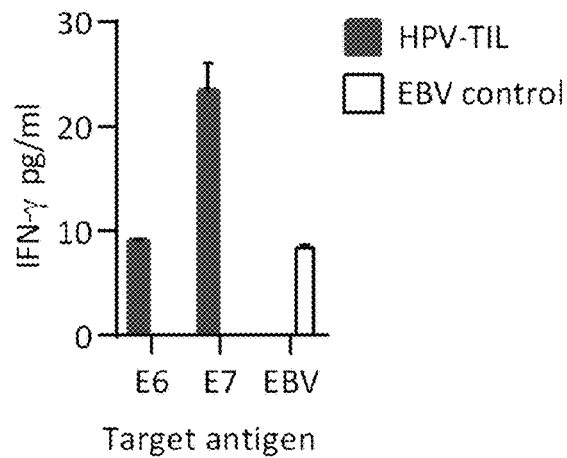
FIGS. 18A-D are graphs showing the reactivity of TIL to be administered to Patient 4 (A and C) or Patient 8 (B and D) (shaded bars) against HPV E6, HPV E7, or Epstein Barr virus (EBV) (control) as measured by IFN-gamma secretion (pg/ml) (A and B) and ELISPOT assays (C and D). Unshaded bars represent the reactivity of EBV-reactive T cells from the same patient (control).
Figure 18B:
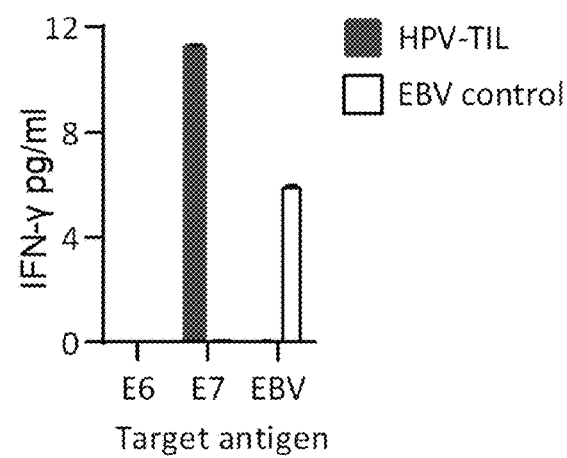
Figure 18C:
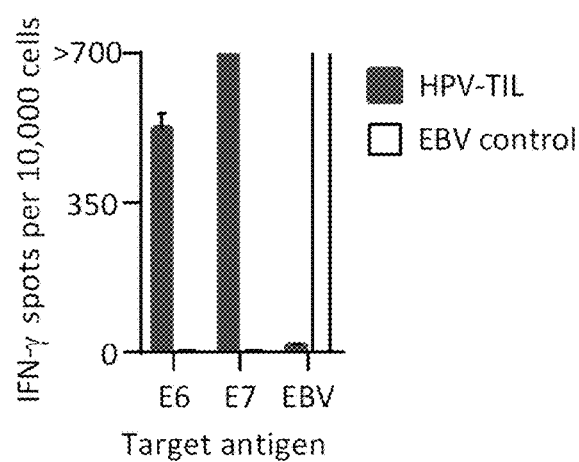
Figure 18D:
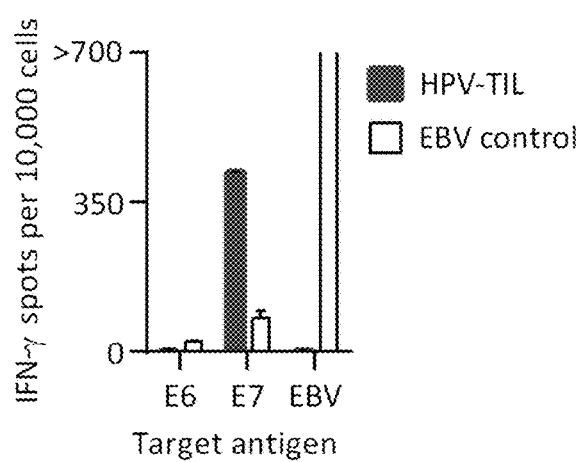

The HPV-TIL administered to Patient 4 were reactive against both the E6 and E7 oncoproteins as demonstrated by interferon (IFN)-γ production and ELISPOT assays (FIGS. 18A and C). Five percent and greater than seven percent of the infused cells showed responses to E6 or E7, respectively by ELISPOT assay (FIGS. 18C and D). E6 responses were CD8+ T cell-mediated, and E7 responses were CD4+ and CD8+ T cell-mediated. In total, 14 percent of the infused cells displayed HPV reactivity as measured by CD137 upregulation assay. For Patient 8, HPV-TIL were reactive against E7 (FIG. 18B), with four percent of T cells responding to the antigen by ELISPOT assay (FIG. 18D). This response was primarily mediated by CD4+ T cells.

Repopulation with Oncoprotein Reactive T Cells

Figure 19A:
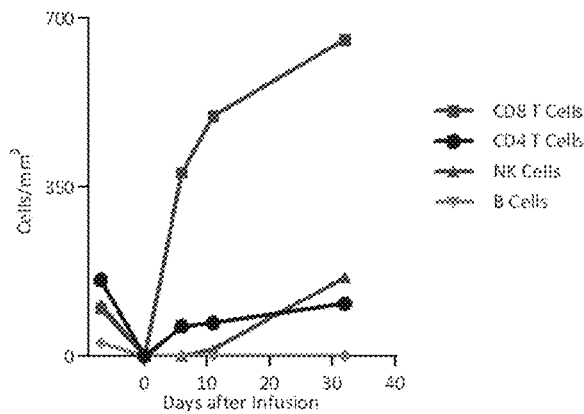
FIGS. 19A-B are graphs showing lymphocyte counts (cells/mm$^3$) for Patient 4 (A) and Patient 8 (B) at various time points (days) after infusion of TIL. Cells counted include CD8 T cells (squares), CD4 T cells (circles), NK cells (▲), and B cells (▼).
Figure 19B:
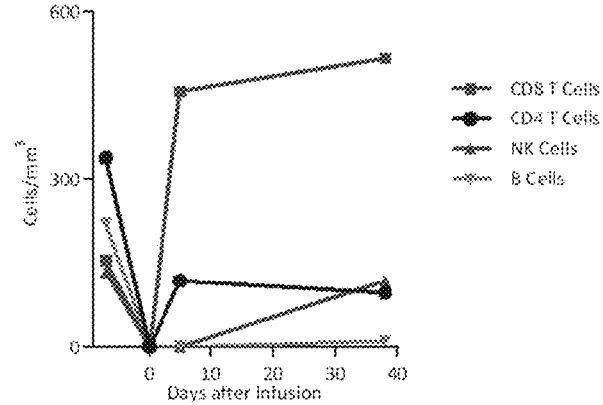
Figure 19C:
FIGS. 19C-D are graphs showing HPV-reactive T cells detected in peripheral blood of Patient 4 (C) or Patient 8 (D) at various time points (months) after infusion of TIL as measured by IFN-gamma (pg/ml). Reactivity against HPV E6 (grey bars), HPV E7 (black bars), or gp100 (control) (unshaded bars) was measured.
Figure 19D:
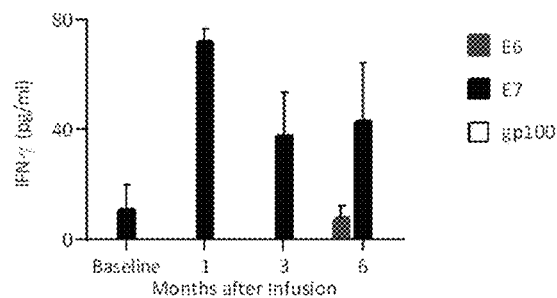
Figure 19E:
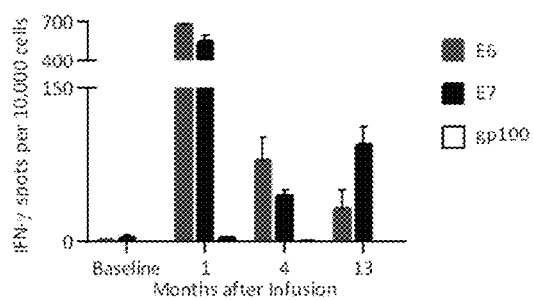
FIGS. 19E-F are graphs showing the quantification of HPV-reactive T cells detected in peripheral blood of Patient 4 (E) or Patient 8 (F) at various time points (months) after infusion of TIL as measured by ELISPOT. Reactivity against HPV E6 (grey bars), HPV E7 (black bars), or gp100 (control) (unshaded bars) was measured.
Figure 19F:
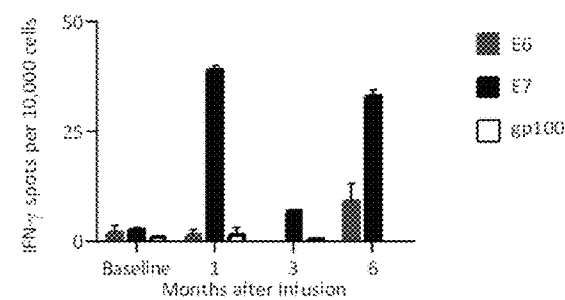
Figure 20A:
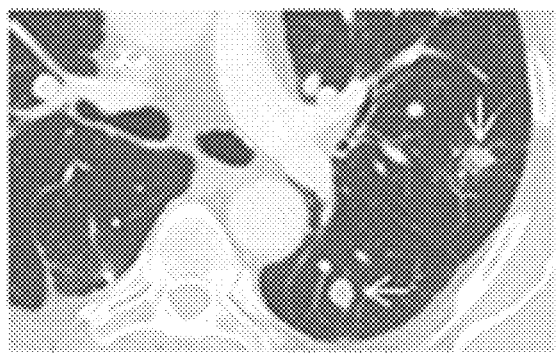
FIGS. 20A-J are magnetic resonance imaging (MRI) scans of Patient 13 who had a metastatic tonsil cancer before (A, C, E, G, and I) and four months after (B, D, F, H, and J) treatment with adoptive cell therapy. The arrows point to multiple malignant tumors in the lungs and the right lung hilum.
Figure 20B:
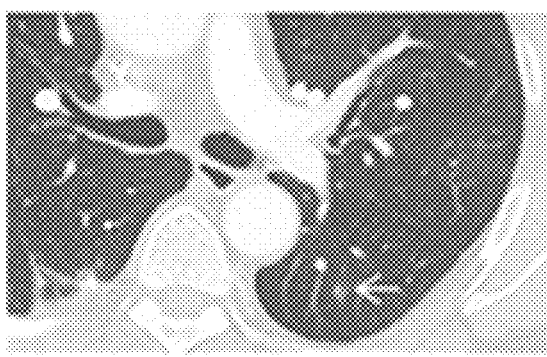
Figure 20C:
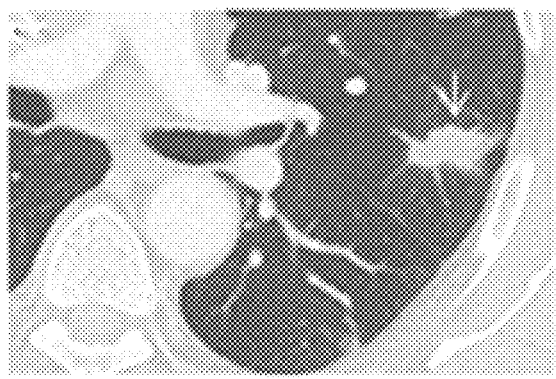
Figure 20D:
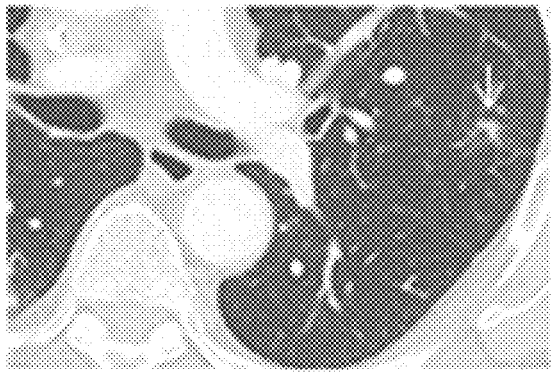
Figure 20E:
Figure 20F:
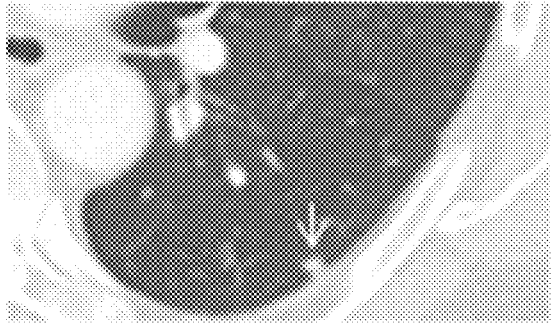
Figure 20G:
Figure 20H:
Figure 20I:
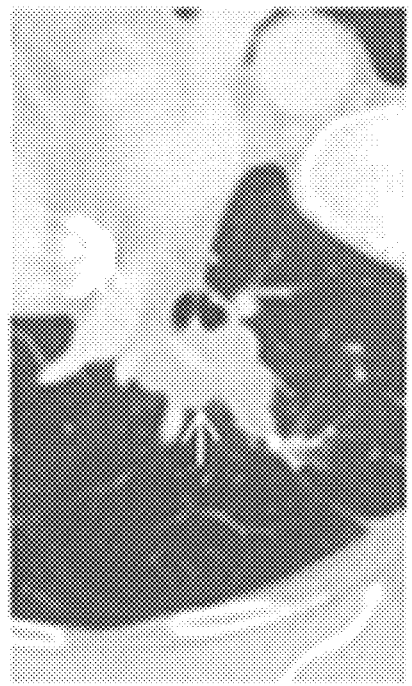
Figure 20J:
Figure 21A:
FIGS. 21A-B are CT scans of the chest of Patient 4 before (A) and 18 months after (B) treatment with adoptive cell therapy. The arrow in A points to a cancerous lesion in a paraaortic lymph node.
Figure 21B:
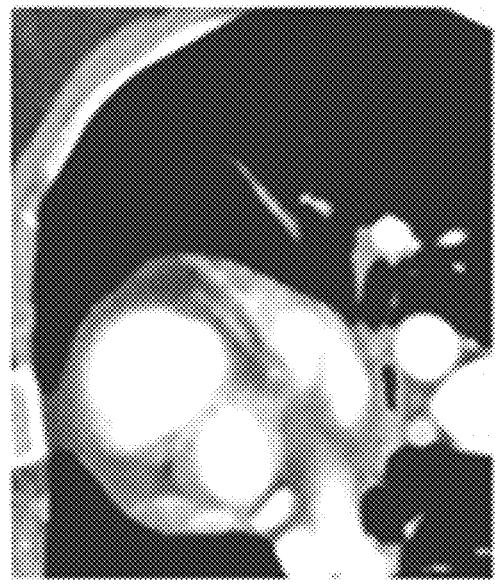
Figure 21C:
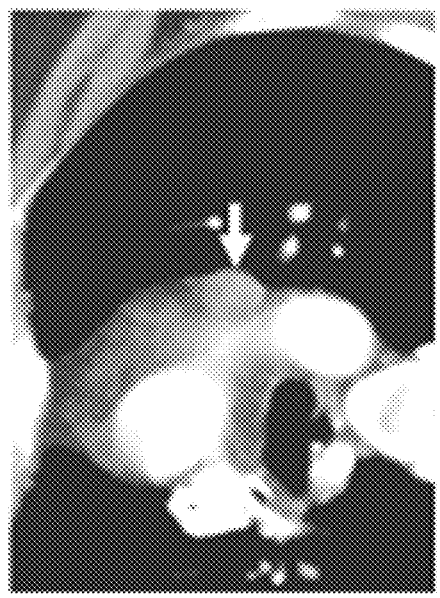
FIGS. 21C-D are CT scans of the chest of Patient 4 before (C) and 18 months after (D) treatment with adoptive cell therapy. The arrows in C point to a left hilar lesion and a subcarinal lesion.
Figure 21D:
Figure 21E:
FIGS. 21E-F are CT scans of the chest of Patient 4 before (E) and 18 months after (F) treatment with adoptive cell therapy. The arrows in E point to bilateral hilar lesions.
Figure 21F:
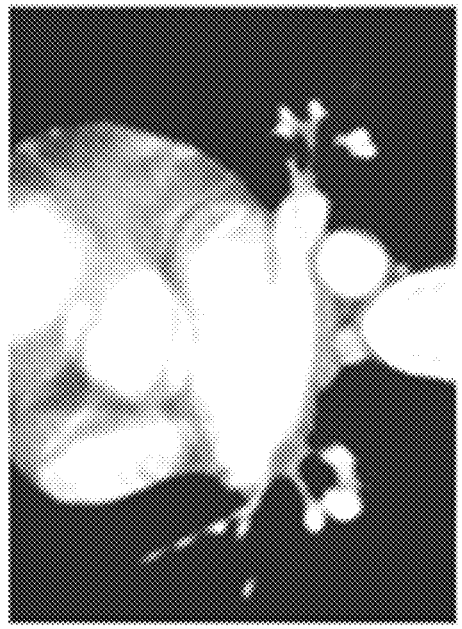
Figure 21G:
FIGS. 21G-H are CT scans of the pelvis of Patient 4 before (G) and 18 months after (H) treatment with adoptive cell therapy. The arrow in G points to a cancerous lesion in the common iliac lymph node.
Figure 21H:
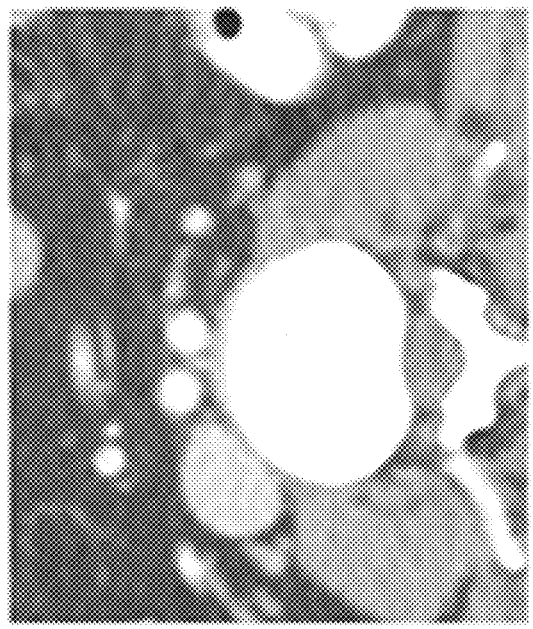
Figure 22A:
FIGS. 22 A-B are CT scans of the abdomen of Patient 8 before (A) and 11 months after (B) treatment with adoptive cell therapy. The arrow in A points to a cancerous lesion in a retroperitoneal lymph node.
FIGS. 22C-D are CT scans of the abdomen of Patient 8 before (C) and 11 months after (D) treatment with adoptive cell therapy. The arrows in C point to a cancerous abdominal wall mass and a retroperitonal tumor.
FIGS. 22E-F are CT scans of the abdomen of Patient 8 before (E) and 11 months after (F) treatment with adoptive cell therapy. The arrow in E points to a cancerous paracolic mass.
FIGS. 22G-H are CT scans of the pelvis of Patient 8 before (G) and 11 months after (H) treatment with adoptive cell therapy. The arrow in G points to a cancerous left pelvic mass. The triangle in H points to an uretal stent.
Figure 22B:
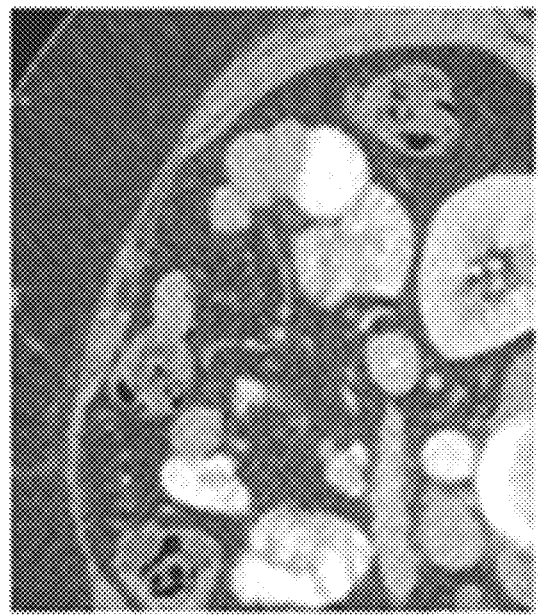
Figure 22C:
Figure 22D:
Figure 22F:
Figure 22H:
Figure 22E:
Figure 22G:
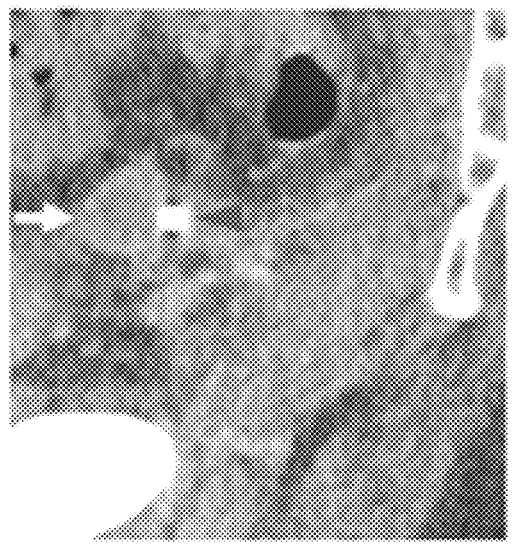

HPV-TIL infusion was followed by rapid increases in peripheral blood CD4+ and CD8+ T cells but not NK and B cells (FIG. 19A-B). Expansion of the numbers of infused T cells was associated with establishment and persistence of peripheral blood T cell reactivity against the HPV oncoproteins as measured by IFN-γ production, ELISPOT, and CD137 upregulation assays (FIG. 19C-F). Both patients had little, if any, reactivity against E6 or E7 prior to treatment. Following treatment, Patient 4 acquired robust T cell recognition of E6 and E7. For Patient 8, this recognition was weaker but nonetheless detectable and, consistent with the infused T cells, directed against only E7. One-month after treatment, 12 percent of Patient 4's peripheral blood T cells were oncoprotein reactive (seven percent against E6 and five percent against E7) (FIG. 19E). Reactivity against these antigens was sustained with one percent of peripheral blood T cells showing oncoprotein recognition four and 13 months after cell infusion (FIG. 19E). Patient 8 showed 0.4 percent HPV reactive T cells one-month after treatment (FIG. 19F). This reactivity was sustained, albeit at lower levels, three and six months after treatment (FIGS. 19 D and F). Consistent with the reactivity of the T cell subsets in the infused HPV-TIL, the HPV specific T cells that repopulated the patients were primarily E6 and E7 reactive CD8+ T cells for Patient 4, and E7 reactive CD4+ T cells for Patient 8.

Example 12

This example provides updated results of Patients 4 and 8 from the clinical study described in Examples 10 and 11 that were obtained four months after the results described in Examples 10 and 11 were obtained. This example demonstrates that adoptive cell therapy using anti-HPV T cells treats cancer.

The objective complete tumor responses of Patients 4 and 8, who were treated as described in Examples 10 and 11, were ongoing 22 and 15 months after treatment, respectively.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating or preventing HPV$^+$ cancer in a patient, the method comprising:
   (a) culturing multiple fragments of an HPV$^+$ tumor sample from the patient in the presence of at least one cytokine;
   (b) obtaining T-cells from the cultured fragments;
   (c) expanding the number of T-cells to produce an expanded population of HPV-specific T-cells using one or both of (i) irradiated allogenic feeder cells and (ii) irradiated autologous feeder cells; and one or both of (iii) OKT3 antibody and (iv) interleukin-2 wherein the T-cells have not been depleted of CD4$^+$ cells;
   (d) optionally, adding a second culturing step following (c); and
   (e) administering the expanded population of HPV-specific T-cells to the patient in an amount effective to treat or prevent the HPV$^+$ cancer in the patient.

2. The method of claim 1, wherein a second culturing step is added after step (c) to further expand the number of selected T-cells.

3. The method of claim 1, wherein the cytokine in step (a) is IL-2.

4. The method of claim 3, wherein the IL-2 in step (a) is present at 6000 IU.

5. The method of claim 1, wherein the IL-2 in step (c) is present at 6000 IU.

6. The method of claim 1, further comprising, prior to step (a), obtaining an HPV$^+$ tumor sample from the patient and fragmenting said tumor samples.

7. The method of claim 6, wherein the tumor samples are fragmented mechanically or enzymatically.

8. The method of claim 1, wherein the expanded population of HPV-specific T-cells recognizes HPV 16-positive cervical cancer cells.

9. The method of claim 1, wherein the expanded population of HPV-specific cells recognizes an HPV antigen selected from the group consisting of HPV 16 E6 and HPV 16 E7.

10. The method of claim 1, wherein the expanded population of HPV-specific cells recognizes an HPV antigen selected from the group consisting of HPV 18 E6 and HPV 18 E7.

11. The method of claim 1, further comprising administering to the patient nonmyleoablative lymphodepleting chemotherapy prior to step (e).

12. The method of claim 1, wherein the expanded population of cells obtained in (d) comprises multiple T-cells having different HPV specificities.

13. The method of claim 1, wherein the expanded population of cells obtained in (d) secretes at least about 200 pg/mL of interferon-y.

14. The method of claim 1, wherein the HPV$^+$ cancer is selected from head and neck squamous cell carcinoma (HNSCC) and cervical cancer.

15. The method of claim 14, wherein the HPV$^+$ cancer is cervical cancer.

16. The method of claim 14, wherein the HPV$^+$ cancer is head and neck squamous cell carcinoma.

17. The method of claim 16, wherein the head and neck squamous cell carcinoma is selected from laryngeal cancer, hypopharyngeal cancer, nasal cavity cancer, nasopharyngeal cancer, oral cancer, oropharyngeal cancer, and salivary gland cancer.

18. The method of claim 1, wherein the expansion step occurs over about 10 to about 14 days.

19. The method of claim 18, wherein the population of HPV-specific T-cells is increased at least about 1000-fold to about 3000-fold.

20. The method of claim 1, wherein the expanded population of HPV-specific T-cells is administered at a dose of from about $1 \times 10^{10}$ to about $13.7 \times 10^{10}$.

21. The method of claim 1, wherein the expanded population of HPV-specific T-cells is administered with a pharmaceutically acceptable carrier.

22. The method of claim 21, wherein the pharmaceutically acceptable carrier is saline, 5% dextrose in water, Ringer's lactate, an electrolyte solution, or PLASMA-LYTE A.

23. The method of claim 1, wherein the expanded population of HPV-specific T-cells is enriched for CD4$^+$ T-cells.

24. The method of claim 1, wherein the culturing step (a) is performed for at least about 12 days.

* * * * *